US009086352B2

(12) United States Patent
Jang et al.

(10) Patent No.: US 9,086,352 B2
(45) Date of Patent: Jul. 21, 2015

(54) STAGE DEVICE AND DRIVING METHOD THEREOF

(71) Applicant: SAMSUNG ELECTRONICS CO., LTD., Suwon-si, Gyeonggi-do (KR)

(72) Inventors: Sang-Don Jang, Suwon-si (KR); Sang-Wook Park, Suwon-si (KR); Oui-Serg Kim, Seongnam-si (KR); Hi-Kuk Lee, Yongin-si (KR); In-Bae Chang, Seoul (KR)

(73) Assignee: Samsung Electronics Co., Ltd., Suwon-si, Gyeonggi-do (KR)

( * ) Notice: Subject to any disclaimer, the term of this patent is extended or adjusted under 35 U.S.C. 154(b) by 59 days.

(21) Appl. No.: 14/094,256

(22) Filed: Dec. 2, 2013

(65) Prior Publication Data

US 2014/0268171 A1    Sep. 18, 2014

(30) Foreign Application Priority Data

Mar. 14, 2013    (KR) .......................... 10-2013-0027525

(51) Int. Cl.
 *G01B 11/02*    (2006.01)
 *G01N 21/00*    (2006.01)

(52) U.S. Cl.
 CPC ...................................... *G01N 21/00* (2013.01)

(58) Field of Classification Search
 CPC ...................................................... G01B 11/04
 USPC ................................................. 356/500, 498
 See application file for complete search history.

(56) References Cited

U.S. PATENT DOCUMENTS

| 4,589,746 | A | * | 5/1986 | Pavone | 396/548 |
|---|---|---|---|---|---|
| 6,331,885 | B1 | | 12/2001 | Nishi | |
| 6,495,847 | B1 | | 12/2002 | Asano et al. | |
| 7,515,277 | B2 | | 4/2009 | Tanaka | |
| 7,903,258 | B2 | | 3/2011 | Bakker | |
| 2001/0035959 | A1 | * | 11/2001 | Hill | 356/500 |
| 2005/0134862 | A1 | * | 6/2005 | Hill | 356/500 |
| 2006/0279743 | A1 | * | 12/2006 | Boesser et al. | 356/500 |
| 2007/0273861 | A1 | | 11/2007 | Sato et al. | |
| 2009/0033899 | A1 | | 2/2009 | Matsuyama et al. | |
| 2013/0016361 | A1 | | 1/2013 | Park et al. | |

FOREIGN PATENT DOCUMENTS

| JP | 09-171954 | 6/1997 |
|---|---|---|
| JP | 2005-345298 | 12/2005 |
| JP | 2010-087310 | 4/2010 |
| KR | 10-2010-0073577 | 7/2010 |
| KR | 10-2013-0008826 | 1/2013 |

* cited by examiner

*Primary Examiner* — Jonathan Hansen
(74) *Attorney, Agent, or Firm* — F. Chau & Associates, LLC

(57) ABSTRACT

A stage device includes a stage configured to move in an X-axis direction and a Y-axis direction, an X-axis interference reflector spaced apart from the stage in the X-axis direction, a first X-axis interferometer disposed on the stage that is configured to measure an X-axis location of the stage using the X-axis interference reflector, and an optical movable element spaced apart from the stage in the Y-axis direction that is configured to shift in the X-axis direction a path of a light beam propagating in the Y-axis direction according to movement of the stage in the X-axis direction.

20 Claims, 15 Drawing Sheets

STAGE DEVICE AND DRIVING METHOD THEREOF

CROSS-REFERENCE TO RELATED APPLICATION

This application claims priority under 35 U.S.C. §119 from Korean Patent Application No. 10-2013-0027525 filed on Mar. 14, 2013 in the Korean Intellectual Property Office (KIPO), and all the benefits accruing therefrom, the contents of which are herein incorporated by reference in their entirety.

BACKGROUND

1. Technical Field

Embodiments of the inventive concept are directed to a stage device that includes an interferometer, and a driving method thereof.

2. Discussion of Related Art

Stage devices are configured to support wafers of semiconductor devices or substrates of display devices. Stages may move the wafers or substrates in an X-axis direction and a Y-axis direction during a fabrication process. The precise control of stage locations in the stage devices during the fabrication process is currently the subject of research.

SUMMARY

Embodiments of the inventive concept provide a stage device capable of accurately measuring a location of a stage, and a driving method thereof.

Other embodiments of the inventive concept provide a stage device capable of precisely controlling a stage, and a driving method thereof.

In accordance with an aspect of the inventive concept, a stage device is provided. The stage device may include: a stage configured to move in an X-axis direction and a Y-axis direction; an X-axis interference reflector spaced apart from the stage in the X-axis direction; a first X-axis interferometer disposed on the stage that is configured to measure an X-axis location of the stage using the X-axis interference reflector; and an optical movable element spaced apart from the stage in the Y-axis direction that is configured to shift in the X-axis direction a path of a light beam propagating in the Y-axis direction according to a movement of the stage in the X-axis direction.

The optical movable element may include an optical body that includes an optical guide groove extending in the X-axis direction, a supporting protrusion coupled to the optical guide groove, a supporting plate coupled to the supporting protrusion, and a driving element configured to move the supporting protrusion along the optical guide groove.

The stage device may further include: a second X-axis interferometer disposed on the stage that is configured to measure the X-axis location of the stage using the X-axis interference reflector; and an X-axis beam splitter disposed on the stage that is configured to distribute a light beam propagating in the Y-axis direction toward the first X-axis interferometer and toward the second X-axis interferometer.

The stage device may further include an X-axis fixed reflector disposed on the stage in a path of a light beam that has propagated through the X-axis beam splitter. The first X-axis interferometer may be disposed on a path of a light beam reflected by the X-axis fixed reflector. The second X-axis interferometer may be disposed on a path of a light beam reflected by the X-axis beam splitter.

An X-axis distance between the first X-axis interference reflector and the second X-axis interferometer may be the same as an X-axis distance between the first X-axis interference reflector and the first X-axis interferometer.

The stage device may further include: a light source spaced from the stage in the Y-axis direction that is configured to emit a beam in the X-axis direction; an optical element mounted on the optical movable element that is configured to distribute the light beam emitted from the light source in the X-axis direction and the Y-axis direction; a Y-axis interference reflector disposed on the stage; and a first Y-axis interferometer spaced apart from the stage in the Y-axis direction that is configured to measure a Y-axis location of the stage using the Y-axis interference reflector. The optical element may include a beam splitter disposed between the light source and the first Y-axis interferometer that is configured to distribute the beam emitted by the light source in the X-axis direction and the Y-axis direction. The first X-axis interferometer may be located between the X-axis interference reflector and the Y-axis interference reflector.

The X-axis interference reflector may extend in the Y-axis direction. The Y-axis interference reflector may extend in the X-axis direction. A horizontal X-axis length of the Y-axis interference reflector may be less than a horizontal Y-axis length of the X-axis interference reflector.

The stage device may further include: a second Y-axis interferometer spaced apart from the stage in the Y-axis direction that is configured to measure the Y-axis location of the stage using the Y-axis interference reflector; and a Y-axis beam splitter spaced apart from the stage in the Y-axis direction that is configured to distribute a beam emitted by the light source in the X-axis direction toward the first Y-axis interferometer and toward the second Y-axis interferometer.

The stage device may further include a Y-axis fixed reflector disposed on a path of a light beam that has propagated through the Y-axis beam splitter. The first Y-axis interferometer may be disposed on a path of a light beam reflected by the Y-axis fixed reflector. The second Y-axis interferometer may be disposed on a path of a light beam reflected by the Y-axis beam splitter.

A Y-axis distance between the Y-axis interference reflector and the second Y-axis interferometer may be the same as a Y-axis distance between the Y-axis interference reflector and the first Y-axis interferometer.

In accordance with an aspect of the inventive concept, a stage device is provided. The stage device may include: a stage that includes a first X-axis interferometer, a first Y-axis interferometer spaced apart from the first X-axis interferometer, and a stage beam splitter configured to distribute a light beam toward the first X-axis interferometer and toward the first Y-axis interferometer; a stage base configured to move the stage in an X-axis direction and a Y-axis direction; a light source disposed on the stage base that is configured to emit a beam in the X-axis direction; a movable reflector disposed on the stage base that is configured to reflect the light beam emitted by the light source in the Y-axis direction; and an optical movable element disposed on the stage base that is configured to move the movable reflector in the X-axis direction. The stage beam splitter may be disposed in a path of the light beam reflected by the movable reflector.

The stage may further include a second Y-axis interferometer spaced apart from the first Y-axis interferometer in the X-axis direction, a Y-axis fixed reflector configured to reflect a light beam to the first Y-axis interferometer, and a Y-axis beam splitter configured to distribute to the second Y-axis interferometer and the Y-axis fixed reflector the light beam propagating toward the first Y-axis interferometer from the stage beam splitter. A virtual line between the first Y-axis interferometer and the second Y-axis interferometer may be parallel to an X-axis side of the stage base.

The stage may further include a second X-axis interferometer spaced apart from the first X-axis interferometer in the Y-axis direction, a X-axis fixed reflector configured to reflect a light beam to the first X-axis interferometer, and a X-axis beam splitter configured to distribute to the second X-axis interferometer and to the X-axis fixed reflector the light beam propagating toward the first X-axis interferometer from the stage beam splitter. A virtual line between the first X-axis interferometer and the second X-axis interferometer may be parallel to a Y-axis side of the stage base.

In accordance with an aspect of the invention, a stage device is provided. The stage device may include: a stage configured to move in an X-axis direction and a Y-axis direction; a stage base configured to move the stage in an X-axis direction and a Y-axis direction; an X-axis interference reflector mounted on the stage base and spaced apart from the stage in the X-axis direction; a first X-axis interferometer disposed on the stage that is configured to measure an X-axis location of the stage using the X-axis interference reflector; a Y-axis interference reflector that extends perpendicular to the X-axis interference reflector; a first Y-axis interferometer configured to measure an Y-axis location of the stage using the Y-axis interference reflector; and a beam splitter configured to distribute a light beam in the X-axis direction toward the first Y-axis interferometer and the Y-axis direction toward the first X-axis interferometer. The beam splitter shifts in the X-axis direction according to a movement of the stage in the X-axis direction.

The Y-axis interference reflector may be disposed on the stage base and may be spaced apart from the stage in the Y-axis direction. The first Y-axis interferometer and the beam splitter may be disposed on the stage.

The stage device mat further include: a second Y-axis interferometer disposed on the stage and spaced apart from the first Y-axis interferometer in the X-axis direction; and a Y-axis beam splitter and a Y-axis fixed reflector each disposed on the stage. The Y-axis beam splitter may be configured to distribute a light beam received from the beam splitter to the second Y-axis interferometer and the Y-axis fixed reflector, and the Y-axis fixed reflector may be configured to reflect a light beam received from the Y-axis beam splitter to the first Y-axis interferometer. A virtual line between the first Y-axis interferometer and the second Y-axis interferometer may be parallel to an X-axis side of the stage base.

The stage device of claim may further include a second X-axis interferometer disposed on the stage and spaced apart from the first X-axis interferometer in the Y-axis direction; and an X-axis beam splitter and an X-axis fixed reflector each disposed on the stage. The X-axis beam splitter may be configured to distribute a light beam received from the beam splitter to the second X-axis interferometer and to the X-axis fixed reflector, and the X-axis fixed reflector may configured to reflect a light beam received from the X-axis beam splitter to the first X-axis. A virtual line between the first X-axis interferometer and the second X-axis interferometer may be parallel to a Y-axis side of the stage base.

The Y-axis interference reflector may be disposed on the stage, the first Y-axis interferometer may be disposed on the stage base and may be spaced apart from the stage in the Y-axis direction. The stage device may further include a movable optical element upon which the beam splitter is mounted that is disposed on the stage base and spaced apart from the stage in a Y-axis direction. The movable optical element may be configured to move in the X-axis direction and the beam splitter may be configured to distribute a light beam received from a light source.

The stage device may further include: a second X-axis interferometer disposed on the stage that is configured to measure the X-axis location of the stage using the X-axis interference reflector; an X-axis beam splitter disposed on the stage that is configured to distribute a light beam received from the beam splitter toward the first X-axis interferometer and toward the second X-axis interferometer; and an X-axis fixed reflector disposed on the stage in a path of a light beam that has propagated through the X-axis beam splitter. The first X-axis interferometer may be disposed on a path of a light beam reflected by the X-axis fixed reflector, and the second X-axis interferometer may be disposed on a path of a light beam reflected by the X-axis beam splitter. An X-axis distance between the first X-axis interference reflector and the second X-axis interferometer may be the same as an X-axis distance between the first X-axis interference reflector and the first X-axis interferometer.

The stage device may further include: a second Y-axis interferometer spaced disposed on the stage base and apart from the stage in the Y-axis direction that is configured to measure the Y-axis location of the stage using the Y-axis interference reflector; a Y-axis beam splitter disposed on the stage base and spaced apart from the stage in the Y-axis direction that is configured to distribute a beam received from the beam splitter in the X-axis direction toward the first Y-axis interferometer and toward the second Y-axis interferometer; and a Y-axis fixed reflector disposed on the stage base on a path of a light beam that has propagated through the Y-axis beam splitter. The first Y-axis interferometer may be disposed on a path of a light beam reflected by the Y-axis fixed reflector, and the second Y-axis interferometer may be disposed on a path of a light beam reflected by the Y-axis beam splitter. A Y-axis distance between the Y-axis interference reflector and the second Y-axis interferometer may be the same as a Y-axis distance between the Y-axis interference reflector and the first Y-axis interferometer.

DETAILED DESCRIPTION OF EXEMPLARY EMBODIMENTS

Figure 1:
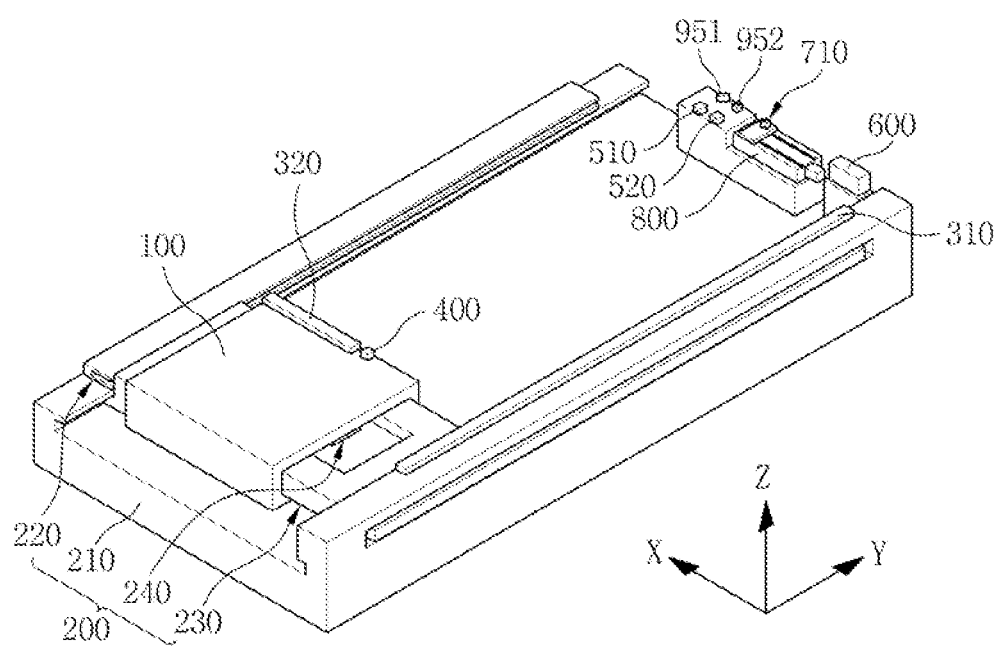
FIG. 1 is a perspective view of a stage device according to an embodiment of the inventive concept.

Various embodiments will now be described more fully with reference to the accompanying drawings in which some embodiments are shown. These inventive concepts may, however, be embodied in different forms and should not be construed as limited to the embodiments set forth herein. Although a few embodiments of the inventive concept have been shown and described, it would be appreciated by those of ordinary skill in the art that changes may be made in these exemplary embodiments without departing from the principles and spirit of the inventive concept, the scope of which is defined in the claims and their equivalents.

Like numerals refer to like elements throughout. In the drawings, the thicknesses of layers and regions may be exaggerated for clarity. Further, it will be understood that when it is described that the first element is disposed "on" a second element, a third element may be disposed between the first element and the second element as well as the first element is disposed on an upper side in direct contact with the second element.

Figure 2:
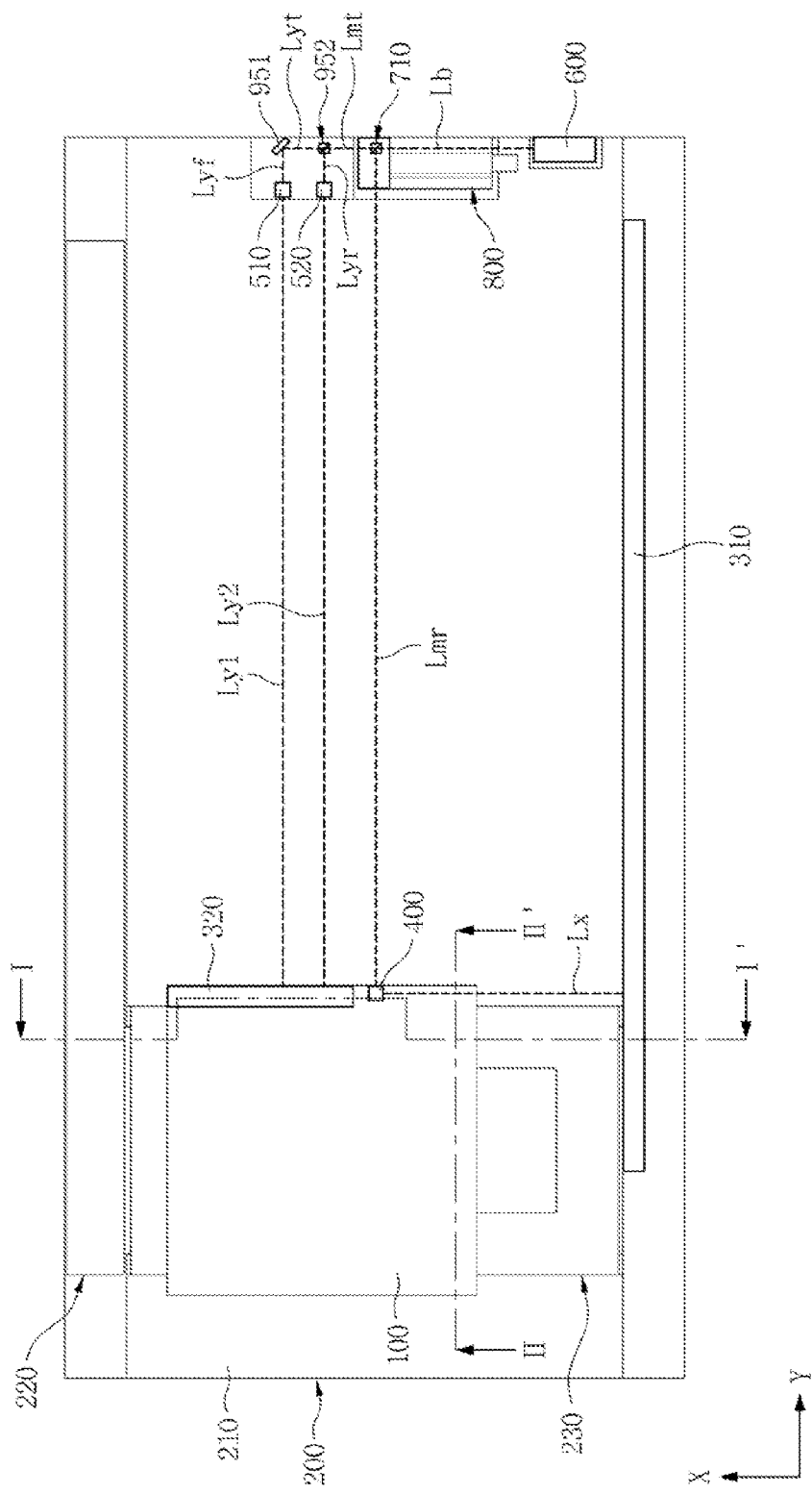
FIG. 2 is a plan view of a stage device according to an embodiment of the inventive concept.
Figure 3A:
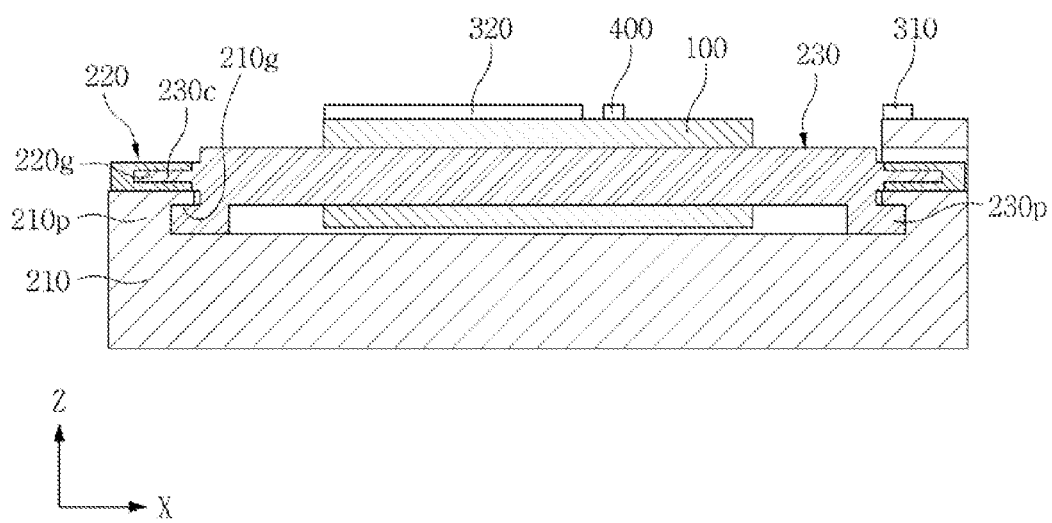
FIG. 3A is a cross-sectional view taken along line I-I' of FIG. 2.
Figure 3B:
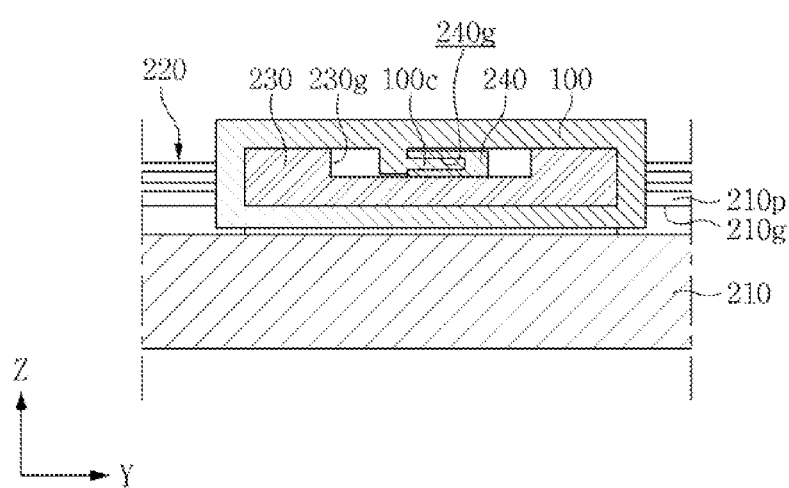
FIG. 3B is a cross-sectional view taken along line II-II' of FIG. 2.

FIG. 1 is a perspective view of a stage device according to an embodiment of the inventive concept. FIG. 2 is a plan view of a stage device according to an embodiment of the inventive concept. FIG. 3A is a cross-sectional view taken along line I-I, and FIG. 3B is a cross-sectional view taken along line II-II'.

Referring to FIGS. 1, 2, 3A, and 3B, a stage device according to an embodiment of the inventive concept may include a stage 100, a stage base 200, an X-axis interference reflector 310, a Y-axis interference reflector 320, an X-axis interferometer 400, a first Y-axis interferometer 510, a second Y-axis interferometer 520, a light source 600, an optical element 710, an optical movable element 800, a Y-axis fixed reflector 951, and a Y-axis beam splitter 952.

The stage 100 may support a semiconductor device or a display device. The stage 100 may support a wafer of the semiconductor device or a substrate of the display device. The substrate of the display device may include a glass substrate or a flexible substrate. The wafer or the substrate may be fixed on the stage 100 during a fabrication process. The stage 100 may be in direct contact with the wafer or the substrate.

The stage base 200 may support the stage 100. The stage 100 may be disposed on an upper surface of the stage base 200. The stage base 200 may move the stage 100. The stage 100 may be moved by the stage base 200 in an X-axis direction and a Y-axis direction. The wafer or the substrate may be moved on the upper surface of the stage base 200 in the X-axis direction and the Y-axis direction.

The stage base 200 may include a base body 210, Y-axis driving elements 220, a guide block 230, and an X-axis driving element 240.

The base body 210 may provide a space on which the stage is to be moved. For example, an upper surface of the base body 210 may be coplanar to an X-Y plane defined by the X-axis direction and the Y-axis direction. The Y-axis driving elements 220, the guide block 230, and the X-axis driving element 240 may be disposed on the upper surface of the base body 210.

The base body 210 may have a rectangular shape. For example, a horizontal X-axis length of the base body 210 may be less than Y-axis length of the base body 210. A Y-axis movement distance of the stage 100 may be greater than X-axis movement distance of the stage 100.

The base body 210 may include body protrusions 210p. The body protrusions 210p may protrude upward from edge portions of the upper surface of the base body 210. The body protrusions 210p may be disposed at opposite sides of the base body 210. For example, the body protrusions 210p may be disposed along the Y-axis sides of the base body 210 and may extend in the Y-axis direction. The body protrusions 210p may be separated from each other in the X-axis direction. A horizontal Y-axis length of each of the body protrusions 210p may be the same a Y-axis length of the base body 210. The stage 100 may be moved between the body protrusions 210p.

Each of the body protrusions 210p may include a block guide groove 210g. The block guide groove 210g may be disposed on a side of a corresponding body protrusion 210p. For example, the block guide groove 210g may be disposed on a side of the corresponding body protrusion 210p facing the stage 100. The block guide groove 210g may face a side of the stage 100. The block guide groove 210g may extend along a surface of the corresponding body protrusion 210p. For example, the block guide groove 210g may extend in the Y-axis direction.

The Y-axis driving elements 220 may move the stage 100 in the Y-axis direction. The wafer or the substrate may be moved in the Y-axis direction by the Y-axis driving elements 220.

The Y-axis driving elements 220 may be disposed on the upper surface of the base body 210. The Y-axis driving elements 220 may be disposed on upper surfaces of the body protrusions 210p. Each of the Y-axis driving elements 220 may be in contact with the upper surface of a corresponding body protrusion 210p. The Y-axis driving elements 220 may extend in the Y-axis direction. The Y-axis driving elements 220 may prevent the stage from coming off of the upper surface of the stage base 200. A horizontal, Y-axis length of each of the Y-axis driving elements 220 may be less than a Y-axis length of the stage base 200. The horizontal Y-axis length of each of the Y-axis driving elements 220 may be less than a Y-axis-length of the base body 210. The horizontal Y-axis length of each of the Y-axis driving elements 220 may be less than a Y-axis-length of each of the body protrusions 210p.

Each of the Y-axis driving elements 220 may include a block coupling groove 220g. The block coupling groove 220g may be disposed in a side of a corresponding Y-axis driving element 220. For example, the block coupling groove 220g may be disposed in a side of the corresponding Y-axis driving element 220 facing the stage 100. The block coupling groove 220g may face the side of the stage 100. The block coupling groove 220g may be disposed above the block guide groove 210g. The block coupling groove 220g may be parallel to the block guide groove 210g. The block coupling groove 220g may extend along a surface of the corresponding Y-axis driving element 220. For example, the block coupling groove 220g may extend in the Y-axis direction.

The guide block 230 may support the stage 100. A bottom surface of the guide block 230 may be spaced upward from the upper surface of the base body 210. The stage 100 may have a shape surrounding the guide block 230.

The guide block 230 may extend in the X-axis direction. The guide block 230 may connect to the body protrusions 210p. The guide block 230 may connect to the Y-axis driving elements 220. A horizontal X-axis length of the stage 100 may be less than an X-axis-length of the guide block 230. The stage 100 may move along the guide block 230 in the X-axis direction.

The guide block 230 may include guide protrusions 230p, guide connection portions 230c, and a stage guide groove 230g.

The guide protrusions 230p may be disposed on sides of the guide block 230 facing the body protrusions 210p. Each of the guide protrusions 230p may extend into the block guide groove 210g of a corresponding body protrusion 210p. The guide protrusions 230p may move along the block guide grooves 210g in the Y-axis direction.

The guide connection portions 230c may be disposed on the sides of the guide block 230 facing the Y-axis driving elements 220. Each of the guide connection portions 230c may extend into the block coupling groove 220g of a corresponding Y-axis driving element 220. Each of the guide connection portions 230c may be coupled to a corresponding block coupling groove 220g. The guide connection portions 230c may be moved by the Y-axis driving elements 220 in the Y-axis direction.

The stage guide groove 230g may be a depression disposed in an upper surface of the guide block 230. The stage guide groove 230g may extend in the same direction as an extending direction of the guide block 230. For example, the stage guide groove 230g may extend in the X-axis direction. A horizontal X-axis length of the stage guide groove 230g may be greater than that of the stage 100. The horizontal X-axis length of the stage guide groove 230g may be less than the X-axis-length of the guide block 230.

The X-axis driving element 240 may move the stage 100 in the X-axis direction. The wafer or the substrate may be moved by the X-axis driving element 240 in the X-axis direction.

The X-axis driving element 240 may be disposed in the stage guide groove 230g. The X-axis driving element 240 may be in direct contact with the guide block 230. The X-axis driving element 240 may be in direct contact with a bottom surface of the stage guide groove 230g. A level of an upper surface of the X-axis driving element 240 may be lower than the level of an upper surface of the guide block 230. The X-axis driving element 240 may be spaced from the stage 100.

The X-axis driving element 240 may extend in the X-axis direction. A horizontal X-axis length of the X-axis driving element 240 may be greater than the X-axis-length of the stage 100. The horizontal X-axis length of the X-axis driving element 240 may be less than the X-axis-length of the stage guide groove 230g. A horizontal Y-axis length of the X-axis driving element 240 may be less than the Y-axis-length of the stage guide groove 230g.

The X-axis driving element 240 may include a stage coupling groove 240g. The stage coupling groove 240g may be disposed in a side of the X-axis driving element 240. The stage coupling groove 240g may extend along the side of the X-axis driving element 240. For example, the stage coupling groove 240g may extend in the X-axis direction.

In a stage device according to an embodiment of the inventive concept, the stage 100 may be coupled to the X-axis driving element 240. For example, the stage 100 may include a stage connection portion 100c. The stage connection portion 100c may extend into the stage guide groove 230g. The stage connection portion 100c may further extend into the stage coupling groove 240g. The stage connection portion 100c may be coupled to the stage coupling groove 240g. The stage connection portion 100c may be moved in the X-axis direction by the X-axis driving element 240.

The X-axis interference reflector 310 may be disposed on the stage base 200. The X-axis interference reflector 310 may be disposed on the upper surface of the base body 210. For example, the X-axis interference reflector 310 may be disposed on an upper surface of one of the Y-axis driving elements 220.

The X-axis interference reflector 310 may be spaced from the stage 100 in the X-axis direction. The X-axis interference reflector 310 may extend parallel to a Y-axis side of the stage 100. The X-axis interference reflector 310 may extend parallel to a Y-axis side of the stage base 200. An upper surface of the X-axis interference reflector 310 may be at the same level as an upper surface of a wafer or substrate on the stage 100.

The X-axis interference reflector 310 may extend in the Y-axis direction. A horizontal Y-axis length of the X-axis interference reflector 310 may be less than the Y-axis length of the base body 210. The horizontal Y-axis length of the X-axis interference reflector 310 may be less than the Y-axis lengths of the Y-axis driving elements 220.

In a stage device according to an embodiment of the inventive concept, the X-axis interference reflector 310 may be disposed on the upper surface of the stage base 200. Therefore, in a stage device according to an embodiment of the inventive concept, the X-axis interference reflector 310 may be unaffected by movement of the stage 100. That is, in a stage device according to an embodiment of the inventive concept, deformation of or damage to the X-axis interference reflector 310 by the movement of the stage 100 may be prevented. Therefore, in a stage device according to an embodiment of the inventive concept, the stage 100 may be more reliably positioned in the X-axis direction.

The Y-axis interference reflector 320 may be disposed on the upper surface of the stage 100. The Y-axis interference reflector 320 may be disposed near a side of the stage 100 perpendicular a side of the stage 100 facing the X-axis interference reflector 310. The Y-axis interference reflector 320 may be disposed close to an X-axis side of the stage 100. For example, the Y-axis interference reflector 320 may be disposed near a side of the stage 100 toward a Y-axis progress direction of the stage 100.

The Y-axis interference reflector 320 may extend parallel to X-axis sides of the stage 100. The Y-axis interference reflector 320 may extend parallel to X-axis sides of the stage base 200.

An upper surface of the Y-axis interference reflector 320 may be at the same level as the upper surface of the X-axis interference reflector 310. The surface level of the Y-axis interference reflector 320 may be the same as the upper surface level of the wafer or the substrate on the stage 100.

The Y-axis interference reflector 320 may extend in the X-axis direction. A horizontal X-axis length of the Y-axis interference reflector 320 may be less than the X-axis length of the stage 100. The horizontal X-axis length of the Y-axis interference reflector 320 may be less than the Y-axis length of the X-axis interference reflector 310.

The X-axis interferometer 400 may measure the X-axis location of the stage 100. The X-axis interferometer 400 may measure the X-axis location of the stage 100 using the X-axis interference reflector 310. For example, the X-axis interferometer 400 may radiate a beam Lx to the X-axis interference reflector 310, and measure the X-axis location of the stage 100 from a frequency or phase change of the beam Lx reflected by the X-axis interference reflector 310. For example, the X-axis interferometer 400 may be configured to emit a beam toward the X-axis interference reflector 310 and a beam toward a reference reflector using, for example, a beam splitter, detect beams reflected from the X-axis interference reflector 310 and the reference reflector using a polarizing plate, compare the beam reflected from the X-axis interference reflector 310 to the beam reflected from the reference reflector, and measure the X-axis location change of the stage 100.

The X-axis interferometer 400 may be disposed on the upper surface of the stage 100. The X-axis interferometer 400 may be disposed near a side of the stage 100 facing the X-axis interference reflector 310. For example, the X-axis interferometer 400 may be disposed between the X-axis interference reflector 310 and the Y-axis interference reflector 320.

In a stage device according to an embodiment of the inventive concept, the X-axis interferometer 400 may be disposed on the upper surface of the stage 100. Therefore, in a stage device according to an embodiment of the inventive concept, an area of the stage 100 and an area of the stage base 200 may be unaffected by a movement distance of the stage 100. Accordingly, in a stage device according to an embodiment of the inventive concept, the total size may be reduced.

The first Y-axis interferometer 510 may measure a Y-axis location of the stage 100. The first Y-axis interferometer 510 may measure the Y-axis location of the stage 100 using the Y-axis interference reflector 320. For example, the first Y-axis interferometer 510 may emit a beam Ly1 to the Y-axis interference reflector 320, and measure the Y-axis location of the stage 100 from a frequency or phase change of the beam Ly1 reflected by the Y-axis interference reflector 320. A structure of the first Y-axis interferometer 510 may be the same as that of the X-axis interferometer 400.

The first Y-axis interferometer 510 may be disposed on the stage base 200. The first Y-axis interferometer 510 may be spaced from the stage 100 in the Y-axis direction. The first Y-axis interferometer 510 may face the Y-axis interference reflector 320. For example, the first Y-axis interferometer 510 may be spaced from the stage 100 in the Y-axis progress direction of the stage 100.

The second Y-axis interferometer 520 may measure the Y-axis location of the stage 100. The second Y-axis interferometer 520 may measure the Y-axis location of the stage 100 using the Y-axis interference reflector 320. For example, the second Y-axis interferometer 520 may emit a beam Ly2 to the Y-axis interference reflector 320, and measure the Y-axis location of the stage 100 from a frequency or phase change of the beam Ly2 reflected by the Y-axis interference reflector 320. A structure of the second Y-axis interferometer 520 may be the same as that of the first Y-axis interferometer 510. The structure of the second Y-axis interferometer 520 may be the same as that of the X-axis interferometer 400.

The second Y-axis interferometer 520 may be disposed on the stage base 200. The second Y-axis interferometer 520 may be spaced from the stage 100 in the Y-axis direction. The second Y-axis interferometer 520 may face the Y-axis interference reflector 320. For example, the second Y-axis interferometer 520 may be spaced from the stage 100 in the Y-axis progress direction of the stage 100.

The second Y-axis interferometer 520 may be spaced from the first Y-axis interferometer 510 in the X-axis direction. For example, a Y-axis distance between the Y-axis interference reflector 320 and the second Y-axis interferometer 520 may be the same as the Y-axis distance between the Y-axis interference reflector 320 and the first Y-axis interferometer 510.

A stage device according to an embodiment of the inventive concept may include the first Y-axis interferometer 510 and the second Y-axis interferometer 520. Therefore, in a stage device according to an embodiment of the inventive concept, the Y-axis location of the stage 100 may be measured at two points. Accordingly, in a stage device according to an embodiment of the inventive concept, torsion of the stage 100 may be measured.

The light source 600 may emit a beam Lb to the X-axis interferometer 400, the first Y-axis interferometer 510, and the second Y-axis interferometer 520. The light source 600 may emit the beam Lb in one direction. For example, the light source 600 may emit the beam Lb in the X-axis direction.

The light source 600 may be spaced from the stage 100. For example, the light source 600 may be spaced from the stage 100 in the Y-axis direction. The light source 600 may be disposed on the stage base 200. The light source 600 may be disposed on the upper surface of the base body 210.

The optical element 710 may distribute the beam Lb emitted by the light source 600. The optical element 710 may distribute the beam Lb emitted from the light source 600 toward the first X-axis interferometer 400 toward the first Y-axis interferometer 510. The optical element 710 may distribute in the X-axis direction and the Y-axis direction the beam Lb emitted by the light source 600. For example, the optical element 710 may include a beam splitter configured to distribute the beam Lb emitted by the light source 600 toward the X-axis interferometer 400, and toward the first Y-axis interferometer 510.

The optical element 710 may be spaced from the stage 100. For example, the optical element 710 may be spaced from the stage 100 in the Y-axis direction. The optical element 710 may be disposed on the upper surface of the base body 210.

The optical element 710 may be disposed on a path of the beam Lb emitted by the light source 600. For example, the optical element 710 may be spaced from the light source 600 in the X-axis direction. The optical element 710 may be disposed between the light source 600 and the first Y-axis interferometer 510. The optical element 710 may be disposed between the light source 600 and the second Y-axis interferometer 520.

The Y-axis fixed reflector 951 may reflect a beam to the first Y-axis interferometer 510. The Y-axis fixed reflector 951 may reflect toward the first Y-axis interferometer 510 a beam Lmt that has propagated through the optical element 710. The first Y-axis interferometer 510 may be disposed on a path of a beam Lyf reflected by the Y-axis fixed reflector 951. For example, the Y-axis fixed reflector 951 may be spaced from the first Y-axis interferometer 510 in the Y-axis direction. The first Y-axis interferometer 510 may be disposed between the Y-axis interference reflector 320 and the Y-axis fixed reflector 951.

The Y-axis fixed reflector 951 may be spaced from the stage 100. For example, the Y-axis fixed reflector 951 may be spaced from the stage 100 in the Y-axis direction. The Y-axis fixed reflector 951 may be disposed on the upper surface of the base body 210.

The Y-axis fixed reflector 951 may be disposed on a path of the beam Lmt emitted toward the first Y-axis interferometer 510 by the optical element 710. The Y-axis fixed reflector 951 may be disposed on a path of the beam Lmt propagating through the optical element 710. For example, the Y-axis fixed reflector 951 may be spaced from the optical element 710 in the X-axis direction. The optical element 710 may be disposed between the light source 600 and the Y-axis fixed reflector 951.

The Y-axis beam splitter 952 may distribute the beam Lmt propagating through the optical element 710. The Y-axis beam splitter 952 may distribute the beam Lmt toward the second Y-axis interferometer 520 and toward the Y-axis fixed reflector 951. For example, the Y-axis beam splitter 952 may distribute the beam Lmt in the X-axis direction and the Y-axis direction. The second Y-axis interferometer 520 may be disposed on a path of a beam Lyr reflected by the Y-axis beam splitter 952.

The Y-axis beam splitter 952 may be spaced from the stage 100. For example, the Y-axis beam splitter 952 may be spaced from the stage 100 in the Y-axis direction. The Y-axis beam splitter 952 may be disposed on the upper surface of the base body 210.

The Y-axis beam splitter 952 may be disposed between the optical element 710 and the Y-axis fixed reflector 951. The Y-axis fixed reflector 951 may be disposed on a path of a beam Lyt that has propagated through the Y-axis beam splitter 952. For example, the Y-axis fixed reflector 951 may be spaced from the Y-axis beam splitter 952 in the X-axis direction. The path of the beam Lyt may be the same as that of the beam Lmt propagating through the optical element 710. The Y-axis fixed reflector 951 may be disposed on the path of the beam Lyt that has propagated through the Y-axis beam splitter 952.

The optical movable element 800 may move the optical element 710. The optical movable element 800 may move the optical element 710 in the X-axis direction. The optical movable element 800 may move the optical element 710 so that the beam Lmr reflected by the optical element 710 is aimed at the X-axis interferometer 400. The optical movable element 800 may move the optical element 710 according to the location of the stage 100. The path of the beam Lmr reflected toward the X-axis interferometer 400 from the optical element 710 may be shifted in the X-axis direction by the optical movable element 800 according to the location of the stage 100 in the X-axis direction.

The optical movable element 800 may be spaced from the stage 100. For example, the optical movable element 800 may be spaced from the stage 100 in the Y-axis direction. The optical movable element 800 may be disposed on the upper surface of the base body 210. The optical movable element 800 may support the optical element 710. The optical movable element 800 may be disposed between the base body 210 and the optical element 710.

Figure 4:
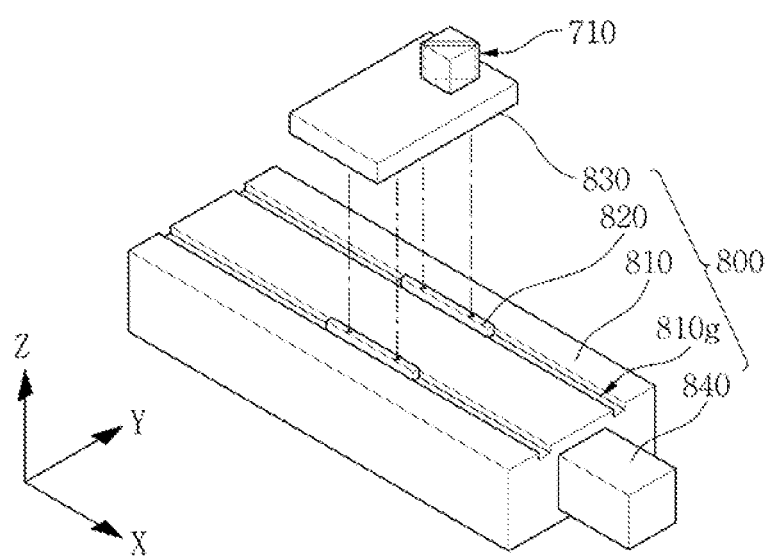
FIG. 4 is an exploded perspective view of an optical movable element of a stage device according to an embodiment of the inventive concept.

FIG. 4 is an exploded perspective view of an optical movable element 800 of a stage device according to an embodiment of the inventive concept.

Referring to FIG. 4, the optical movable element 800 of the stage device according to an embodiment of the inventive concept may include an optical body 810, supporting protrusions 820, a supporting plate 830, and a driving element 840.

The optical body 810 may be in contact with the base body 210. The optical body 810 may include optical guide grooves 810g. The optical guide grooves 810g may extend in the X-axis direction. The optical guide grooves 810g may be disposed on an upper surface of the optical body 810.

The supporting protrusions 820 may be disposed in the optical guide grooves 810g. The supporting protrusions 820 may move along the optical guide grooves 810g. An upper surface level of the supporting protrusions 820 may be higher than the upper surface level of the optical body 810.

The supporting plate 830 may support the optical element 710. The supporting plate 830 may be disposed on the upper surfaces of the supporting protrusions 820. The supporting protrusions 820 may support the supporting plate 830. The supporting plate 830 may be fixed to the upper surfaces of the supporting protrusions 820.

The driving element 840 may move the supporting protrusions 820. The driving element 840 may move the supporting protrusions 820 in the X-axis direction according to the X-axis location of the stage 100. The driving element 840 may be operated in conjunction with the X-axis driving element 240. An X-axis movement distance of the supporting protrusion 820 may be the same as the X-axis movement distance of the stage 100.

Figure 5:
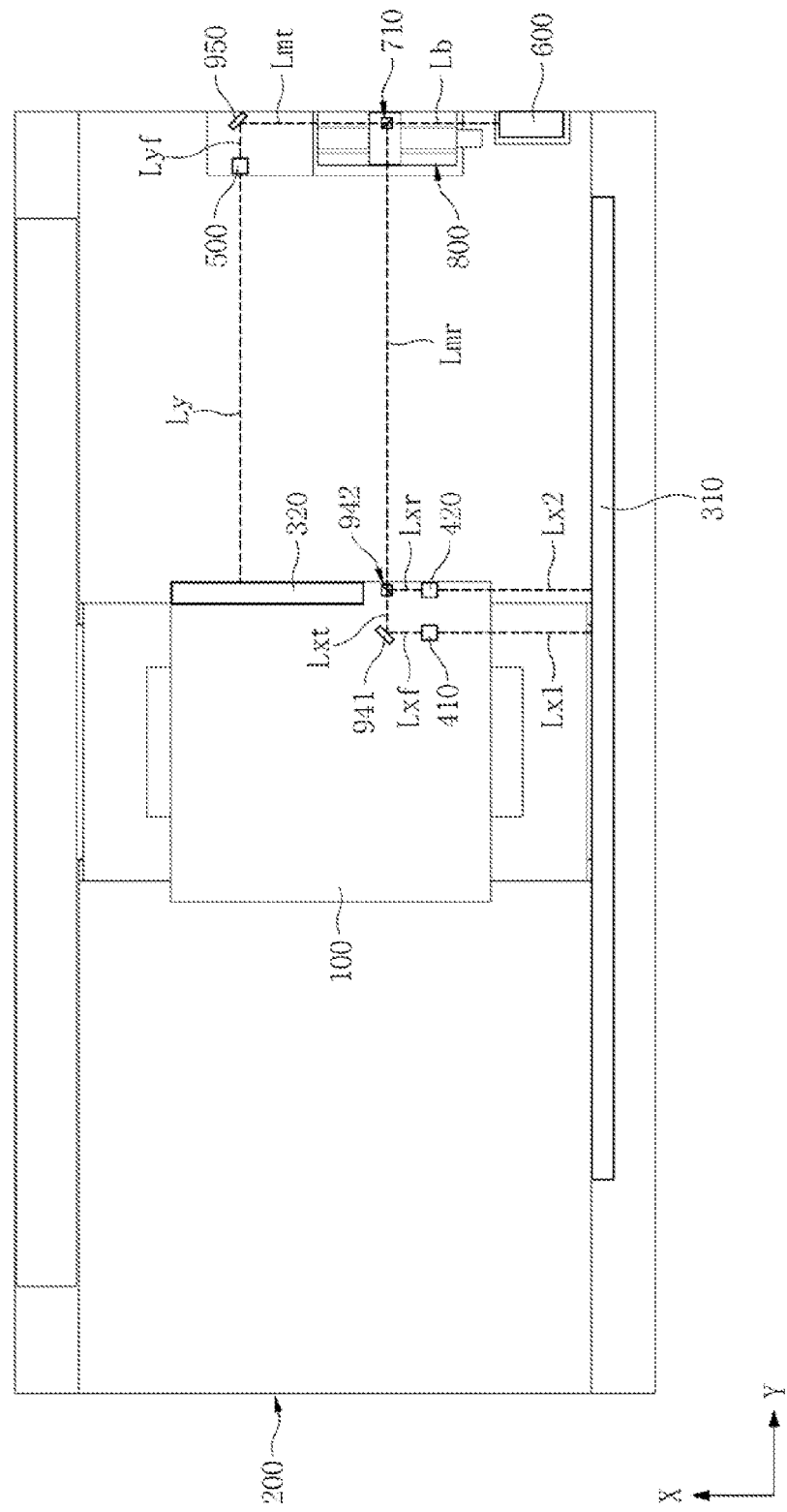
FIG. 5 is a plan view of a stage device according to another embodiment of the inventive concept.

FIG. 5 is a plan view of a stage device according to an embodiment of the inventive concept.

Referring to FIG. 5, a stage device according to an embodiment of the inventive concept may include a stage 100, a stage base 200, an X-axis interference reflector 310, a Y-axis interference reflector 320, a first X-axis interferometer 410, a second X-axis interferometer 420, a Y-axis interferometer 500, a light source 600, an optical element 710, an optical movable element 800, an X-axis fixed reflector 941, an X-axis beam splitter 942, and a Y-axis fixed reflector 950.

The first X-axis interferometer 410 may measure an X-axis location of the stage 100. The first X-axis interferometer 410 may measure the X-axis location of the stage 100 using the X-axis interference reflector 310. For example, the first X-axis interferometer 410 may emit a beam Lx1 to the X-axis interference reflector 310, and measure the X-axis location of the stage 100 from a frequency or phase change of the beam Lx1 reflected by the X-axis interference reflector 310.

The first X-axis interferometer 410 may be disposed on an upper surface of the stage 100. The first X-axis interferometer 410 may be disposed close to a side of the stage 100 facing the X-axis interference reflector 310. For example, the first X-axis interferometer 410 may be disposed between the X-axis interference reflector 310 and the Y-axis interference reflector 320.

The second X-axis interferometer 420 may measure the X-axis location of the stage 100. The second X-axis interferometer 420 may measure the X-axis location of the stage 100 using the X-axis interference reflector 310. For example, the second X-axis interferometer 420 may emit a beam Lx2 to the X-axis interference reflector 310, and measure the X-axis location of the stage 100 from a frequency or phase change of the beam Lx2 reflected by the X-axis interference reflector 310. A structure of the second X-axis interferometer 420 may be the same as that of the first X-axis interferometer 410.

The second X-axis interferometer 420 may be disposed on the upper surface of the stage 100. The second X-axis interferometer 420 may be disposed close to the side of the stage 100 facing the X-axis interference reflector 310. For example, the second X-axis interferometer 420 may be disposed between the X-axis interference reflector 310 and the Y-axis interference reflector 320.

The second X-axis interferometer 420 may be spaced from the first X-axis interferometer 410 in the Y-axis direction. For example, an X-axis distance between the X-axis interference reflector 310 and the second X-axis interferometer 420 may be the same as the X-axis distance between the X-axis interference reflector 310 and the first X-axis interferometer 410.

The Y-axis interferometer 500 may measure a Y-axis location of the stage 100. The Y-axis interferometer 500 may measure the Y-axis location of the stage 100 using the Y-axis interference reflector 320. For example, the Y-axis interferometer 500 may emit a beam Ly to the Y-axis interference reflector 320, and measure the Y-axis location of the stage 100 from a frequency or phase change of the beam Ly reflected by the Y-axis interference reflector 320. A structure of the Y-axis interferometer 500 may be the same as that of the first X-axis interferometer 410. The structure of the Y-axis interferometer 500 may be the same as that of the second X-axis interferometer 420.

The Y-axis interferometer 500 may be disposed on the stage base 200. The Y-axis interferometer 500 may be spaced from the stage 100 in the Y-axis direction. The Y-axis interferometer 500 may face the Y-axis interference reflector 320.

For example, the Y-axis interferometer 500 may be spaced from the stage 100 in the Y-axis progress direction of the stage 100.

The X-axis fixed reflector 941 may reflect toward the first X-axis interferometer 410 a beam Lmr reflected by the optical element 710. The first X-axis interferometer 410 may be disposed on a path of a beam Lxf reflected by the X-axis fixed reflector 941. For example, the X-axis fixed reflector 941 may be spaced from the first X-axis interferometer 410 in the X-axis direction.

The X-axis fixed reflector 941 may be disposed on the upper surface of the stage 100. The first X-axis interferometer 410 may be disposed between the X-axis interference reflector 310 and the X-axis fixed reflector 941.

The X-axis fixed reflector 941 may be disposed on a path of the beam Lmr reflected by the optical element 710. For example, the X-axis fixed reflector 941 may be spaced from the optical element 710 in the Y-axis direction.

The X-axis beam splitter 942 may distribute the beam Lmr reflected by the optical element 710. The X-axis beam splitter 942 may distribute the beam Lmr toward the second X-axis interferometer 420 and the X-axis fixed reflector 941. For example, the X-axis beam splitter 942 may distribute the beam Lmr in the X-axis direction and the Y-axis direction. The second X-axis interferometer 420 may be disposed on a path of a beam Lxr reflected by the X-axis beam splitter 942.

The X-axis beam splitter 942 may be disposed on the upper surface of the stage 100. The second X-axis interferometer 420 may be disposed between the X-axis interference reflector 310 and the X-axis beam splitter 942.

The X-axis beam splitter 942 may be disposed between the optical element 710 and the X-axis fixed reflector 941. The X-axis fixed reflector 941 may be disposed on a path of a beam Lxt that has propagated through the X-axis beam splitter 942. For example, the X-axis fixed reflector 941 may be spaced from the X-axis beam splitter 942 in the Y-axis direction. The path of the beam Lxt may be the same as that of the beam Lmr reflected by the optical element 710. The X-axis fixed reflector 941 may be disposed on the path of the beam Lxt that has propagated through the X-axis beam splitter 942.

The Y-axis fixed reflector 950 may reflect toward the Y-axis interferometer 500 a beam Lmt that has propagated through the optical element 710. The Y-axis interferometer 500 may be disposed on a path of a beam Lyf reflected by the Y-axis fixed reflector 950. For example, the Y-axis fixed reflector 950 may be spaced from the Y-axis interferometer 500 in the Y-axis direction. The Y-axis interferometer 500 may be disposed between the Y-axis interference reflector 320 and the Y-axis fixed reflector 950.

The Y-axis fixed reflector 950 may be spaced from the stage 100. For example, the Y-axis fixed reflector 950 may be spaced from the stage 100 in the Y-axis direction. The Y-axis fixed reflector 950 may be disposed on the upper surface of the stage base 200.

The Y-axis fixed reflector 950 may be disposed on a path of a beam Lmt that has propagated through the optical element 710. For example, the Y-axis fixed reflector 950 may be spaced from the optical element 710 in the X-axis direction. The optical element 710 may be disposed between the light source 600 and the Y-axis fixed reflector 950.

Figure 6:
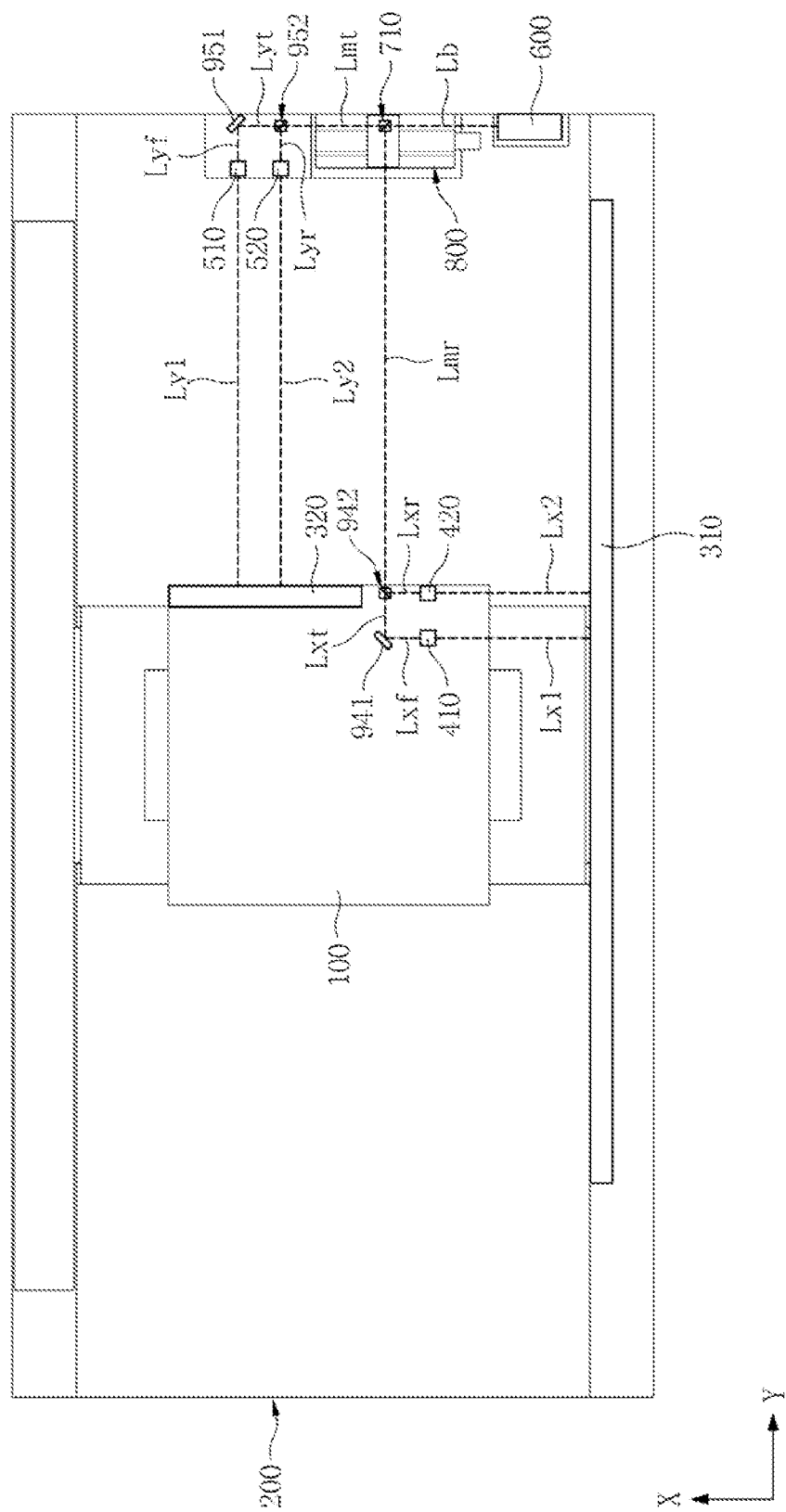
FIG. 6 is a plan view of a stage device according to another embodiment of the inventive concept.

FIG. 6 is a plan view of a stage device according to an embodiment of the inventive concept.

Referring to FIG. 6, a stage device according to an embodiment of the inventive concept may include a stage 100, a stage base 200, an X-axis interference reflector 310, a Y-axis interference reflector 320, a first X-axis interferometer 410, a second X-axis interferometer 420, a first Y-axis interferometer 510, a second Y-axis interferometer 520, a light source 600, an optical element 710, an optical movable element 800, an X-axis fixed reflector 941, an X-axis beam splitter 942, a Y-axis fixed reflector 951, and a Y-axis beam splitter 952.

The X-axis interference reflector 310, the first Y-axis interferometer 510, the second Y-axis interferometer 520, the light source 600, the optical element 710, the optical movable element 800, the Y-axis fixed reflector 951, and the Y-axis beam splitter 952 may be disposed on the stage base 200.

The Y-axis interference reflector 320, the first X-axis interferometer 410, the second X-axis interferometer 420, the X-axis fixed reflector 941, and the X-axis beam splitter 942 may be disposed on the stage 100.

The first X-axis interferometer 410 may be disposed on a path of a beam Lxf reflected by the X-axis fixed reflector 941. The second X-axis interferometer 420 may be disposed on a path of a beam Lxr reflected by the X-axis beam splitter 942. The first Y-axis interferometer 510 may be disposed on a path of a beam Lyf reflected by the Y-axis fixed reflector 951. The second Y-axis interferometer 520 may be disposed on a path of a beam Lyr reflected by the Y-axis beam splitter 952. The optical element 710 may be disposed on a path of a beam Lb emitted by the light source 600. The X-axis fixed reflector 941 may be disposed on a path of a beam Lxt that has propagated through the X-axis beam splitter 942. The X-axis beam splitter 942 may be disposed on a path of a beam Lmr reflected by the optical element 710. The Y-axis fixed reflector 951 may be disposed on a path of a beam Lyt that has propagated through the Y-axis beam splitter 952. The Y-axis beam splitter 952 may be disposed on a path of a beam Lmt that has propagated through the optical element 710.

Figure 7:
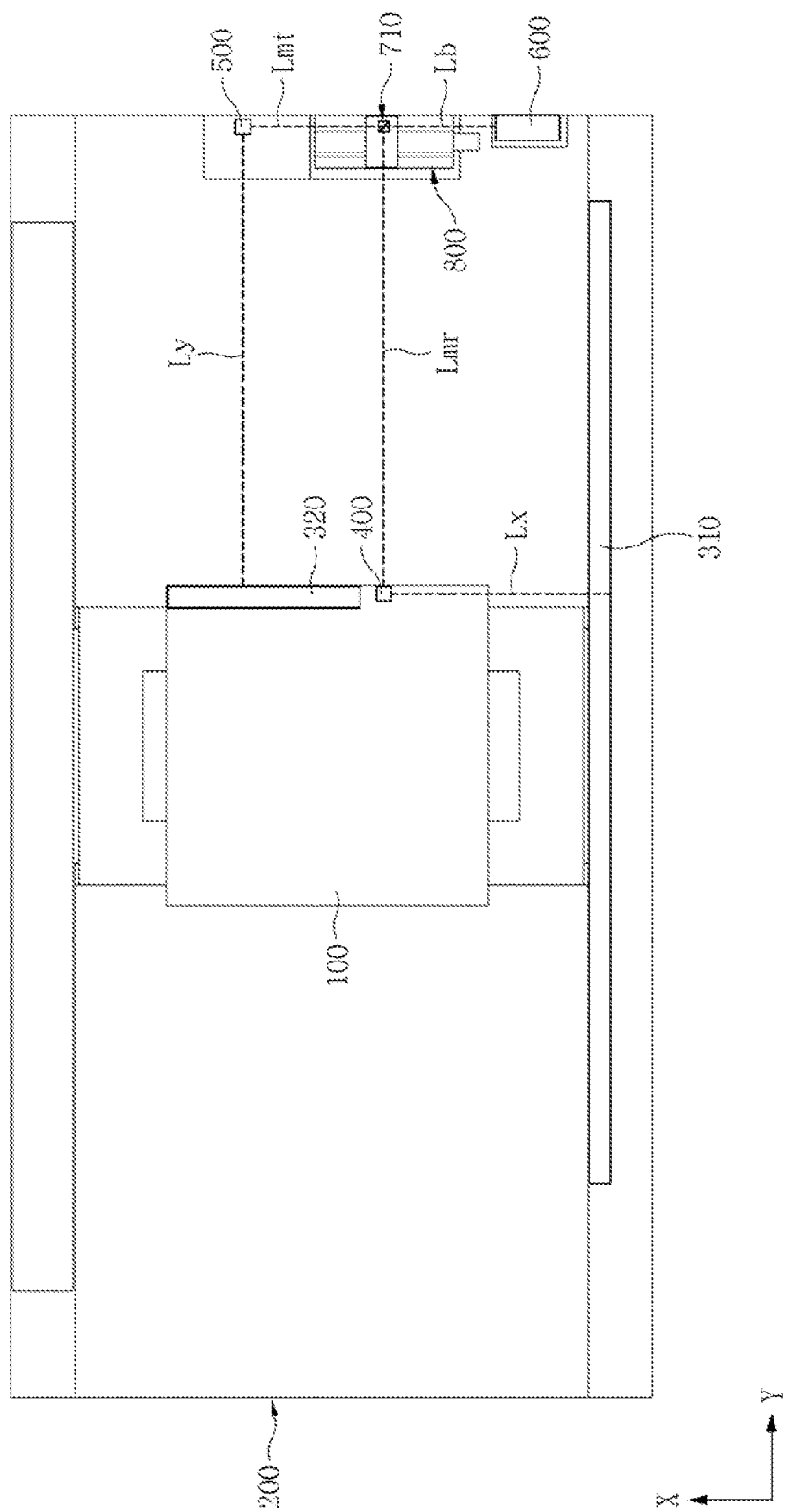
FIG. 7 is a plan view of a stage device according to another embodiment of the inventive concept.

FIG. 7 is a plan view of a stage device according to an embodiment of the inventive concept.

Referring to FIG. 7, a stage device according to an embodiment of the inventive concept may include a stage 100, a stage base 200, an X-axis interference reflector 310, a Y-axis interference reflector 320, an X-axis interferometer 400, a Y-axis interferometer 500, a light source 600, an optical element 710, and an optical movable element 800.

The X-axis interferometer 400 may be disposed on a path of a beam Lmr reflected by the optical element 710. The Y-axis interferometer 500 may be disposed on a path of a beam Lmt that has propagated through the optical element 710.

Figure 8:
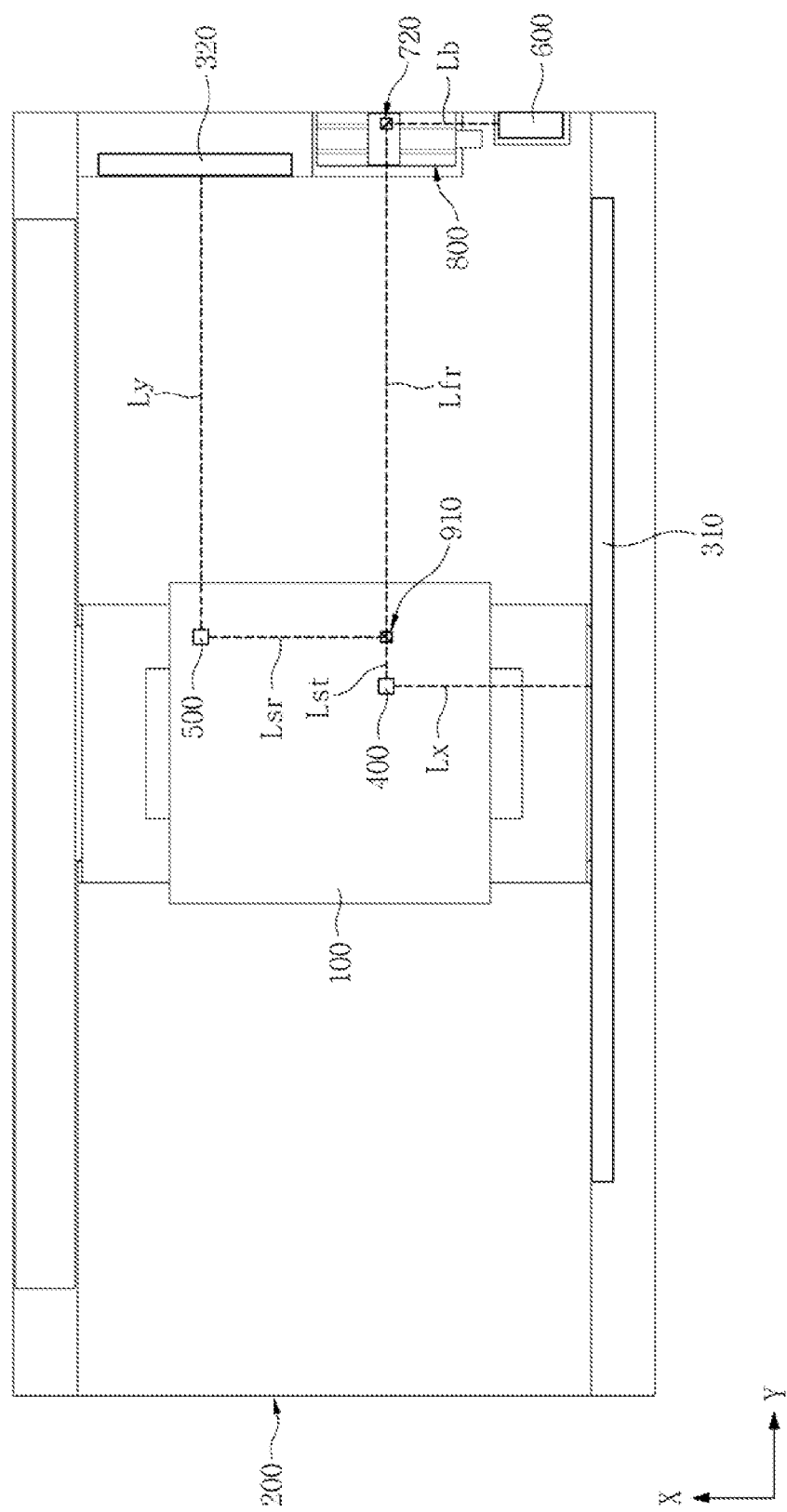
FIG. 8 is a plan view of a stage device according to another embodiment of the inventive concept.

FIG. 8 is a plan view of a stage device according to an embodiment of the inventive concept.

Referring to FIG. 8, a stage device according to an embodiment of the inventive concept may include a stage 100, a stage base 200, an X-axis interference reflector 310, a Y-axis interference reflector 320, an X-axis interferometer 400, a Y-axis interferometer 500, a light source 600, a movable reflector 720, an optical movable element 800, and a stage beam splitter 910.

The Y-axis interference reflector 320 may be disposed on the stage base 200. The Y-axis interference reflector 320 may be spaced from the stage 100 in the Y-axis direction. For example, the Y-axis interference reflector 320 may be spaced from the stage 100 in the Y-axis progress direction of the stage 100.

The X-axis interferometer 400 may be disposed on an upper surface of the stage 100. The X-axis interferometer 400 may be disposed close to a side of the stage 100 facing the X-axis interference reflector 310.

The Y-axis interferometer 500 may be disposed on the upper surface of the stage 100. The Y-axis interferometer 500 may be disposed close to a side of the stage 100 facing the Y-axis interference reflector 320.

The Y-axis interferometer 500 may be spaced from the X-axis interferometer 400 in the X-axis direction. The X-axis interferometer 400 may be disposed between the X-axis interference reflector 310 and the Y-axis interferometer 500.

The movable reflector 720 may reflect toward the stage 100 a beam Lb emitted by the light source 600. For example, the movable reflector 720 may reflect in a Y-axis direction the beam Lb emitted by the light source 600.

The movable reflector 720 may be disposed on a path of the beam Lb radiated by light source 600. For example, the movable reflector 720 may be spaced from the light source 600 in the X-axis direction.

The movable reflector 720 may be disposed on an upper surface of the stage base 200. The movable reflector 720 may be spaced from the stage 100. The movable reflector 720 may be spaced from the stage 100 in the Y-axis direction.

The movable reflector 720 may be moved by the optical movable element 800. The movable reflector 720 may be disposed on the optical movable element 800. The optical movable element 800 may move the movable reflector 720 in an X-axis direction according to movement of the stage 100.

The stage beam splitter 910 may distribute in the X-axis direction and the Y-axis direction a beam Lfr reflected by the movable reflector 720. The stage beam splitter 910 may distribute the beam Lfr in a direction toward the X-axis interferometer 400 and a direction toward the Y-axis interferometer 500. For example, the X-axis interferometer 400 may be disposed on a path of a beam Lst that has propagated through the stage beam splitter 910. The Y-axis interferometer 500 may be disposed on a path of a beam Lsr reflected by the stage beam splitter 910.

The stage beam splitter 910 may be disposed on the upper surface of the stage 100. The stage beam splitter 910 may be disposed on a path of a beam Lfr reflected by the movable reflector 720. The stage beam splitter 910 may be disposed between the X-axis interferometer 400 and the movable reflector 720. The path of the beam Lst that has propagated though the stage beam splitter 910 may be an extension of the path of the beam Lfr reflected by the movable reflector 720. The X-axis interferometer 400 may be disposed on the path of the beam Lfr reflected by the movable reflector 720.

Figure 9:
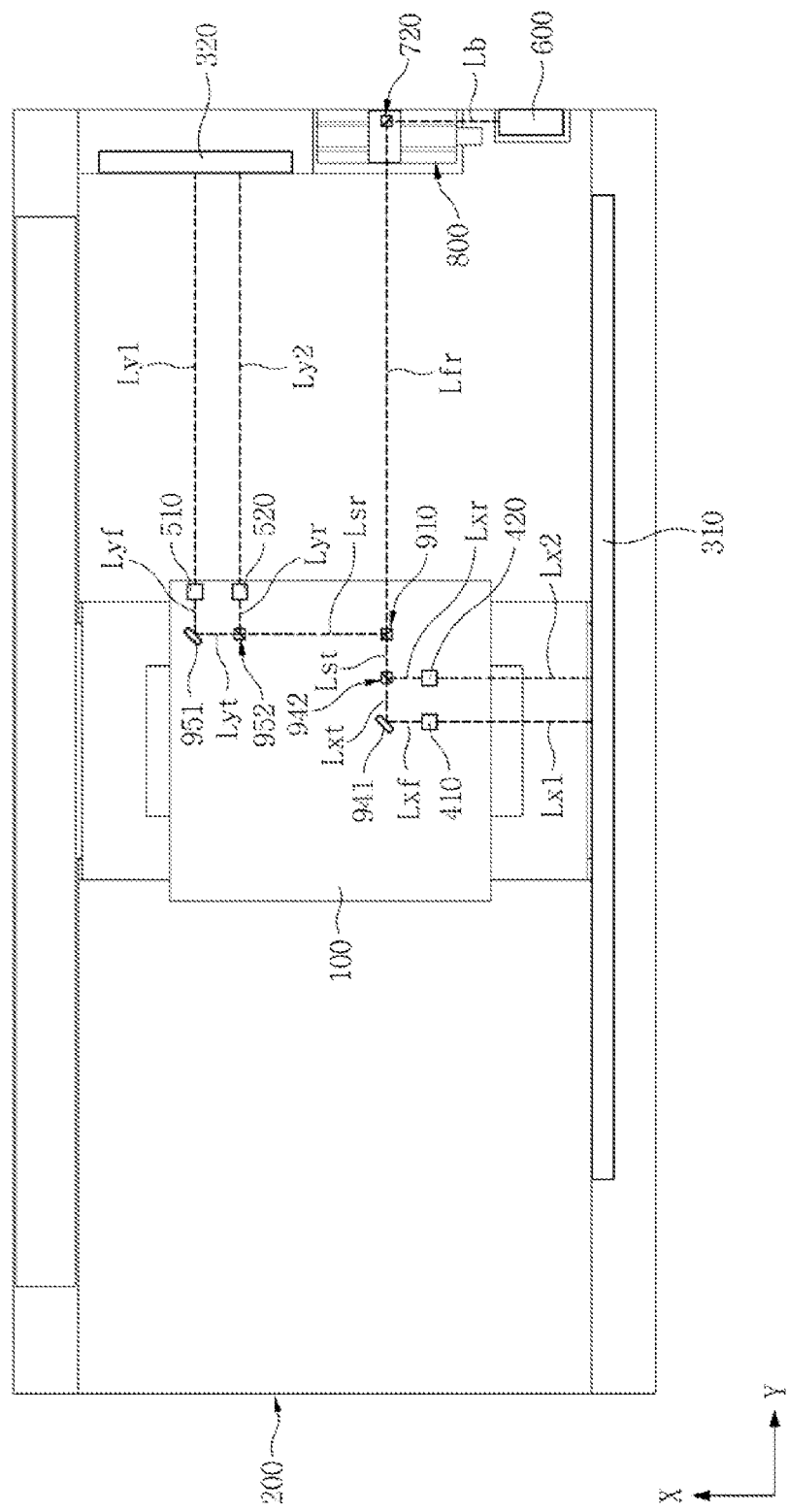
FIG. 9 is a plan view of a stage device according to another embodiment of the inventive concept.

FIG. 9 is a plan view of a stage device according to an embodiment of the inventive concept.

Referring to FIG. 9, a stage device according to an embodiment of the inventive concept may include a stage 100, a stage base 200, an X-axis interference reflector 310, a Y-axis interference reflector 320, a first X-axis interferometer 410, a second X-axis interferometer 420, a first Y-axis interferometer 510, a second Y-axis interferometer 520, a light source 600, a movable reflector 720, an optical movable element 800, a stage beam splitter 910, an X-axis fixed reflector 941, an X-axis beam splitter 942, a Y-axis fixed reflector 951, and a Y-axis beam splitter 952.

The X-axis interference reflector 310, the Y-axis interference reflector 320, the light source 600, the movable reflector 720, and the optical movable element 800 may be disposed on the stage base 200.

The first X-axis interferometer 410, the second X-axis interferometer 420, the first Y-axis interferometer 510, the second Y-axis interferometer 520, the stage beam splitter 910, the X-axis fixed reflector 941, the X-axis beam splitter 942, the Y-axis fixed reflector 951, and the Y-axis beam splitter 952 may be disposed on the stage 100.

The first X-axis interferometer 410 may be disposed on a path of a beam Lxf reflected by the X-axis fixed reflector 941. The second X-axis interferometer 420 may be disposed on a path of a beam Lxr reflected by the X-axis beam splitter 942.

The first Y-axis interferometer 510 may be disposed on a path of a beam Lyf reflected by the Y-axis fixed reflector 951. The second Y-axis interferometer 520 may be disposed on a path of a beam Lyr reflected by the Y-axis beam splitter 952. The movable reflector 720 may be disposed on a path of a beam Lb emitted by the light source 600. The stage beam splitter 910 may be disposed on a path of a beam Lfr reflected by movable reflector 720. The X-axis fixed reflector 941 may be disposed on a path of a beam Lxt that has propagated through the X-axis beam splitter 942. The X-axis beam splitter 942 may be disposed on a path of a beam Lst that has propagated through the stage beam splitter 910. The Y-axis fixed reflector 951 may be disposed on a path of a beam Lyt that has propagated through the Y-axis beam splitter 952. The Y-axis beam splitter 952 may be disposed on a path of a beam Lsr reflected by the stage beam splitter 910.

Figure 10A:
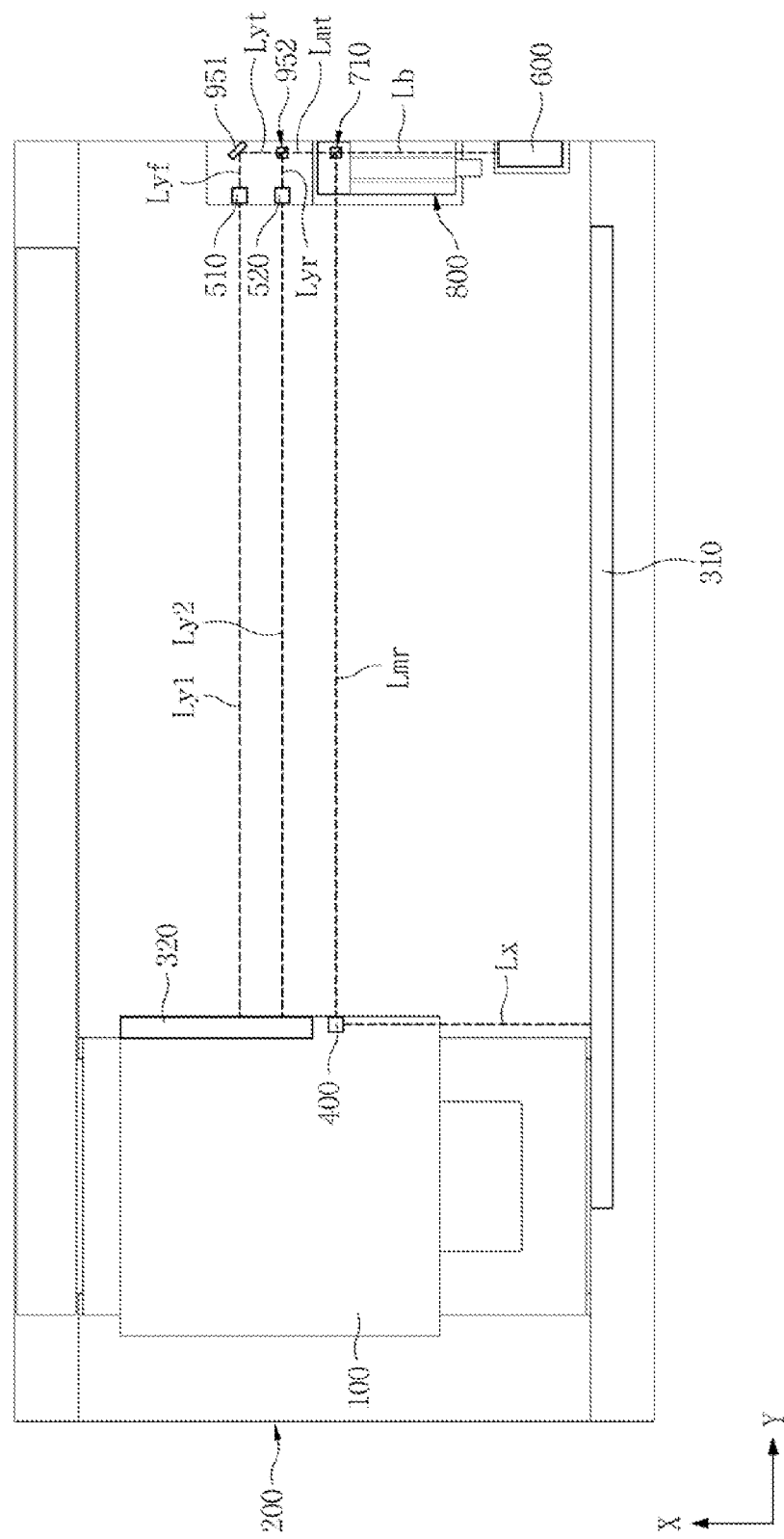
FIGS. 10A to 10C are plan views that sequentially illustrate a method of driving a stage device according to an embodiment of the inventive concept.
Figure 10B:
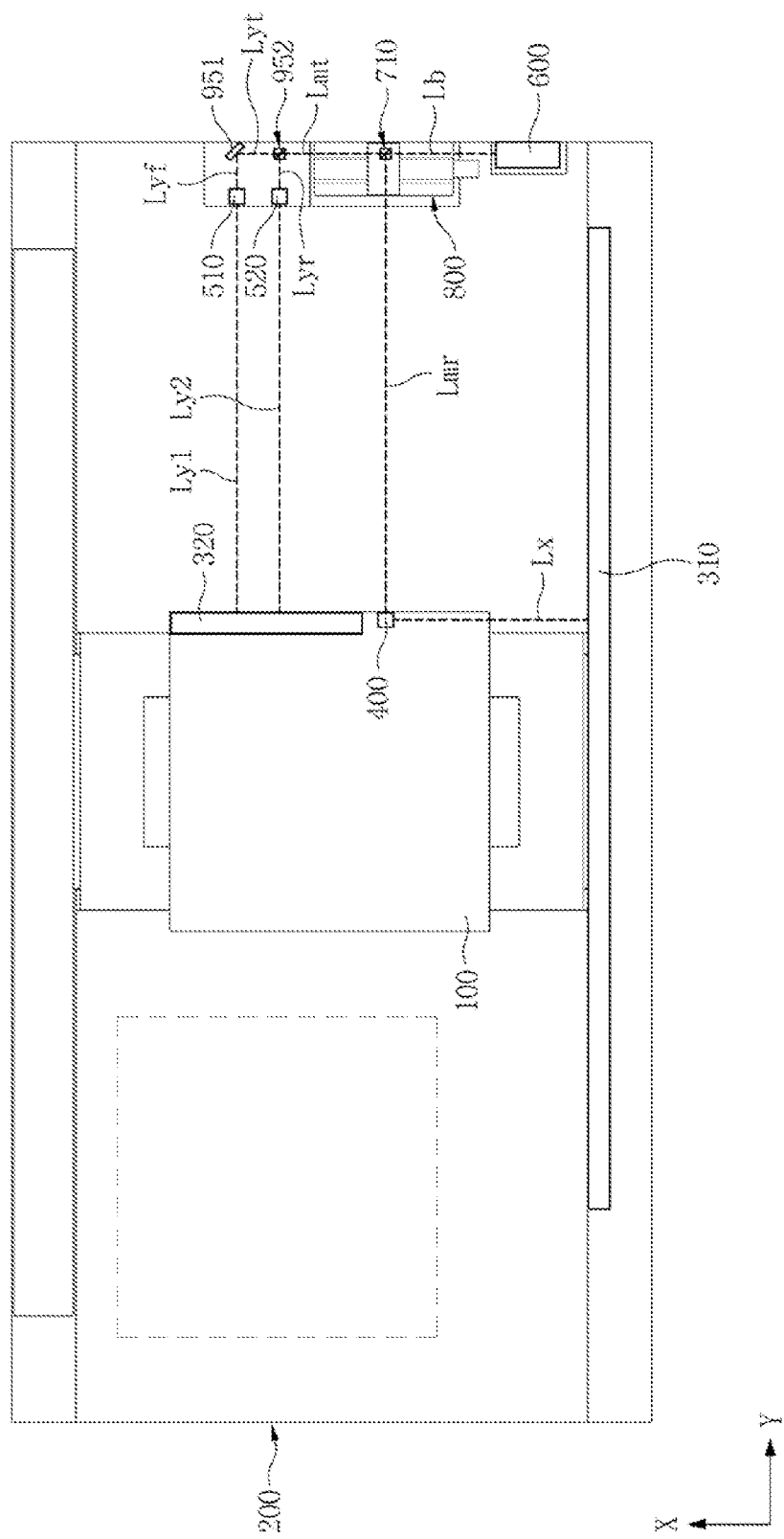
Figure 10C:
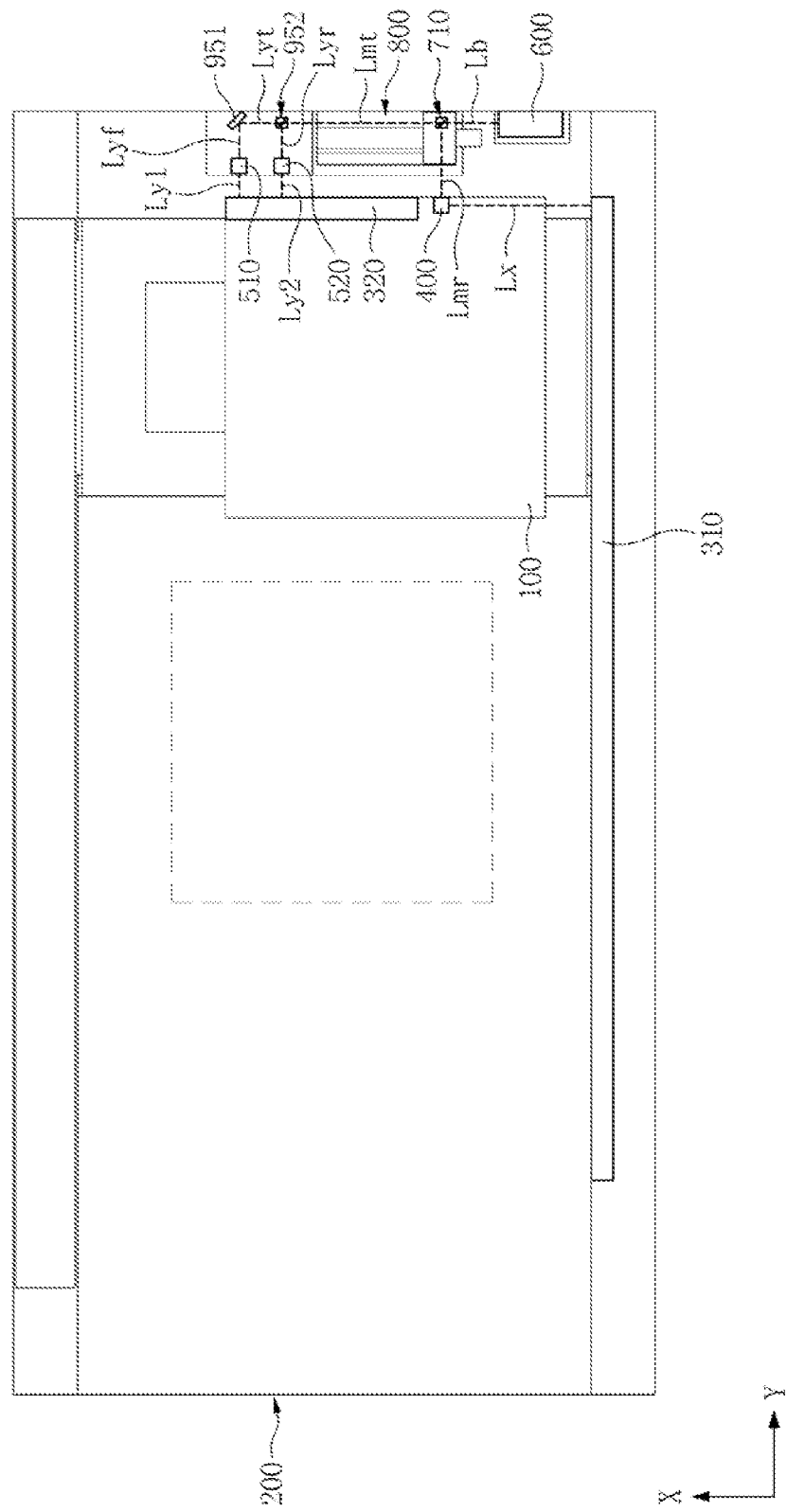

FIGS. 10A to 10C are plan views sequentially illustrating a driving method of driving a stage device according to an embodiment of the inventive concept.

A method of driving a stage device according to an embodiment of the inventive concept will be described with reference to FIGS. 10A to 10C. First, referring to FIG. 10A, the driving method of a stage device according to an embodiment of the inventive concept may include moving the stage 100 to a first stage location, and moving the optical element 710 to a first optical location.

The first stage location of the stage 100 may be spaced far from the X-axis interference reflector 310. The first stage location of the stage 100 may be spaced far from the first Y-axis interferometer 510. The first stage location of the stage 100 may be spaced far from the second Y-axis interferometer 520.

The first optical location of the optical element 710 may be a location from which a beam Lmr reflected by the optical element 710 can propagate to the X-axis interferometer 400 on the stage 100. The X-axis interferometer 400 on the stage 100 located at the first stage location may be located on a path of beam Lmr reflected by the optical element 710 located at the first optical location.

The first optical location of the optical element 710 may be spaced far from the light source 600. The first optical location of the optical element 710 may be close to the second Y-axis interferometer 520.

Referring to FIG. 10B, the driving method of a stage device according to an embodiment of the inventive concept may include having the stage base 200 move the stage 100 to a second stage location and the optical movable element 800 move the optical element 710 to a second optical location.

The second stage location of the stage 100 may be closer to the X-axis interference reflector 310 than the first stage location. The second stage location of the stage 100 may be closer to the first Y-axis interferometer 510 than the first stage location. The second stage location of the stage 100 may be a closer to the second Y-axis interferometer 520 than the first stage location.

The second optical location of the optical element 710 may be a location from which the beam Lmr reflected by the optical element 710 can propagate to the X-axis interferometer 400 on the stage 100 located at the second stage location. The X-axis interferometer 400 on the stage 100 located at the second stage location may be located on a path of the beam Lmr reflected by the optical element 710 located at the second optical location.

The second optical location of the optical element 710 may be closer to the light source 600 than the first optical location.

The second optical location of the optical element 710 may be farther from the second Y-axis interferometer 520 than the first optical location.

Referring to FIG. 10C, the driving method of a stage device according to an embodiment of the inventive concept may include having the stage base 200 move the stage 100 to a third stage location by, and the optical movable element 800 move the optical element 710 to a third optical location.

The third stage location of the stage 100 may be closer to the X-axis interference reflector 310 than the second stage location. The third stage location of the stage 100 may be a closest location to the X-axis interference reflector 310. The third stage location of the stage 100 may be closer to the first Y-axis interferometer 510 than the second stage location. The third stage location of the stage 100 may be a closest location to the first Y-axis interferometer 510. The third stage location of the stage 100 may be closer to the second Y-axis interferometer 520 than the second stage location. The third stage location of the stage 100 may be a closest location to the second Y-axis interferometer 520.

The third optical location of the optical element 710 may be a location from which the beam Lmr reflected by the optical element 710 can propagate to the X-axis interferometer 400 on the stage 100 located at the third stage location. The X-axis interferometer 400 on the stage 100 located at the third stage location may be located on a path of the beam Lmr reflected by the optical element 710 located at the third optical location.

The third optical location of the optical element 710 may be s closer to the light source 600 than the second optical location. The third optical location of the optical element 710 may be a closest location to the light source 600. The third optical location of the optical element 710 may be farther from the second Y-axis interferometer 520 than the second optical location. The third optical location of the optical element 710 may be a farthest location from the second Y-axis interferometer 520.

Figure 11:
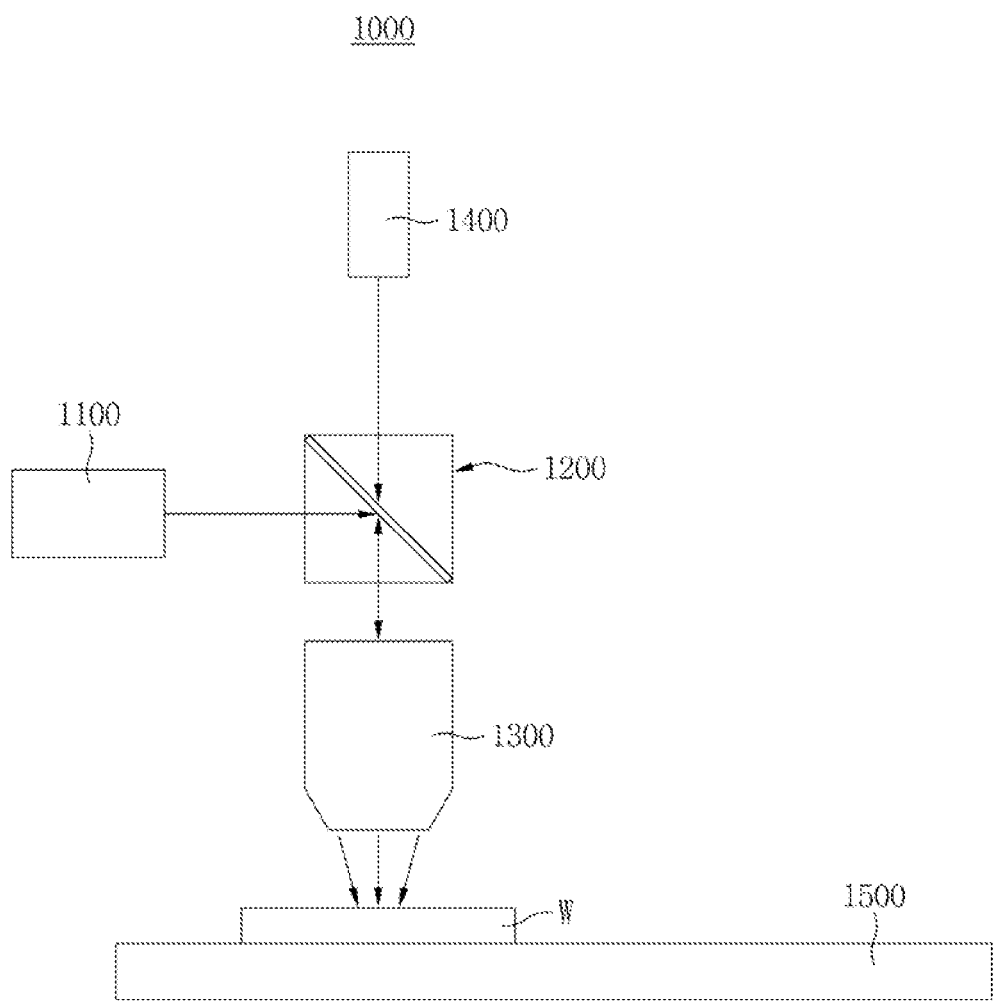
FIG. 11 is a schematic diagram of an inspection apparatus that includes a stage device according to an embodiment of the inventive concept.

FIG. 11 is a schematic diagram of an inspection apparatus that includes a stage device according to an embodiment of the inventive concept.

Referring to FIG. 11, an inspection apparatus 1000 including a stage device according to an embodiment of the inventive concept may include a light source element 1100, a beam splitter 1200, an inspection optical system 1300, a detector 1400, and a stage element 1500.

The inspection apparatus 1000 may be a semiconductor fabrication apparatus. For example, the inspection apparatus 1000 may be an optical inspection apparatus configured to inspect a surface of a wafer of a semiconductor device. The inspection apparatus 1000 may be a display fabrication apparatus. For example, the inspection apparatus 1000 may be an optical inspection apparatus configured to inspect a surface defect of a substrate of a display device.

The light source element 1100 may emit light to a wafer W or a substrate through the beam splitter 1200 and the inspection optical system 1300. The beam splitter 1200 may reflect light of the light source element 1100 toward the wafer W or the substrate. The beam splitter 1200 may transmit light reflected by the wafer W or the substrate. The inspection optical system 1300 may collect light reflected by the beam splitter 1200 to the wafer W or the substrate. Light reflected by the wafer W or the substrate may propagate through the beam splitter 1200. The detector 1400 may inspect the surface of the wafer W or the substrate using light reflected by the wafer W or the substrate. The detector 1400 may detect a pattern defect formed on the wafer W or the substrate using light reflected by the wafer W or the substrate.

The stage element 1500 may support the wafer W or the substrate. The wafer W or the substrate may be fixed on the stage element 1500. The stage element 1500 may move the wafer W or the substrate during a fabrication process. The stage element 1500 may include any one of stage devices according to various embodiments of the inventive concept such as those described above. Therefore, the stage element 1500 may precisely control the wafer W or the substrate. Accordingly, an inspection apparatus 1000 according to an embodiment of the inventive concept may have a more reliable wafer or substrate surface inspection.

Figure 12:
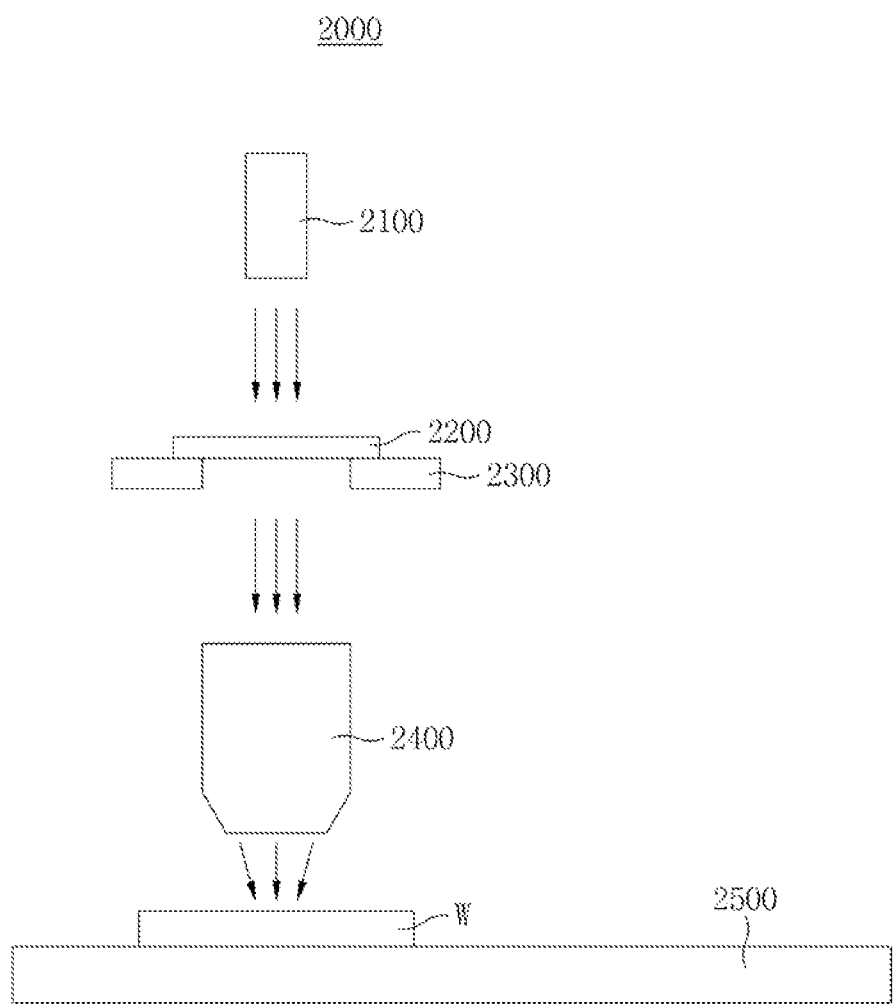
FIG. 12 is a schematic diagram of an exposure apparatus that includes a stage device according to an embodiment of the inventive concept.

FIG. 12 is a schematic diagram of an exposure apparatus according to a stage device according to an embodiment of the inventive concept.

Referring to FIG. 12, an exposure apparatus 2000 that includes a stage device according to an embodiment of the inventive concept may include a light source element 2100, a reticle 2200, a reticle table 2300, an exposure optical system 2400, and a stage element 2500. The exposure apparatus 2000 may be a semiconductor fabrication apparatus. The exposure apparatus 2000 may be a display fabrication apparatus.

The light source element 2100 may emit light to a wafer W or a substrate through the reticle 2200 and the exposure optical system 2400. The reticle 2200 may be disposed between the light source element 2100 and the stage element 2500. The reticle 2200 may include a constant pattern. Light emitted by the light source element 2100 may be patterned by the pattern of the reticle 2200. The light source element 2100 may transfer the pattern of the reticle 2200 to the wafer W or the substrate. The reticle table 2300 may be disposed below the reticle 2200. The reticle table 2300 may support the reticle 2200. The reticle table 2300 may be in direct contact with the reticle 2200. The exposure optical system 2400 may focus the light that has propagsated through the reticle 2200 onto the wafer W or the substrate.

The stage element 2500 may fix the wafer W or the substrate. The stage element 2500 may be disposed below the exposure optical system 2400. The stage element 2500 may move the wafer W or the substrate during a fabrication process. The stage element 2500 may include any one of stage devices according to various embodiments of the inventive concept, such as those described above. Therefore, the stage element 2500 may precisely control the wafer W or the substrate. Accordingly, in the exposure apparatus 2000 according to an embodiment of the inventive concept, reliability of an exposure process may be improved.

Figure 13:
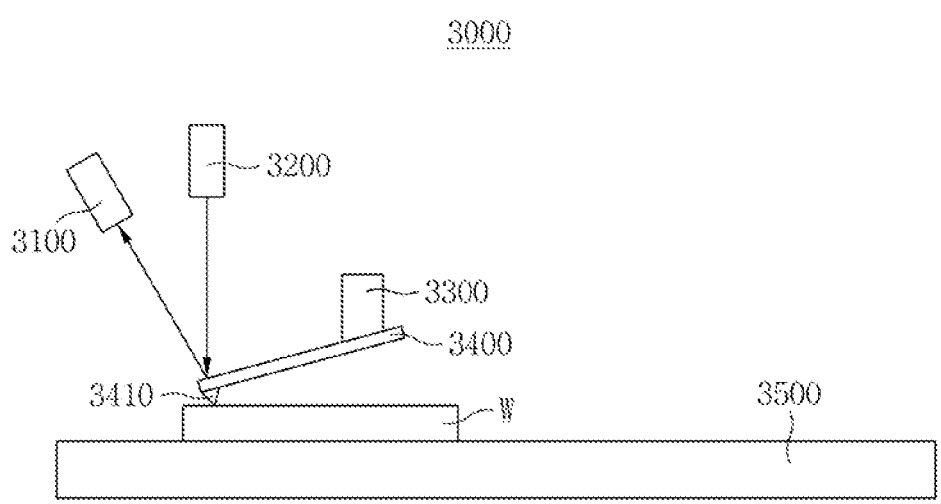
FIG. 13 is a schematic diagram of a measurement apparatus that includes a stage device according to an embodiment of the inventive concept.

FIG. 13 is a schematic diagram of a measurement apparatus that includes a stage device according to an embodiment of the inventive concept.

Referring to FIG. 13, a measurement apparatus 3000 that includes a stage device according to an embodiment of the inventive concept may include a light source element 3100, a light detection element 3200, a cantilever supporting element 3300, a cantilever 3400, and a stage element 3500. The measurement apparatus 3000 may be an atomic microscope such as a scanning probe microscope (SPM). For example, the measurement apparatus 3000 may be an atomic force microscope (AFM).

The light source element 3100 may emit light onto an end of the cantilever 3400. The light detection element 3200 may detect a beam reflected from the cantilever 3400. The light detection element 3200 may measure a surface of a wafer W or a substrate from a wavelength, phase, intensity, or location change of the light reflected from the cantilever 3400. The cantilever supporting element 3300 may fix a location of the cantilever 3400. The cantilever 3400 may include a tip 3410 disposed close to the wafer W or the substrate. The tip 3410 may vertically vibrate according to a surface state of the wafer W or the substrate. The tip 3410 may be spaced from the surface of the wafer W or the substrate.

The stage element 3500 may fix the wafer W or the substrate. The stage element 3500 may move the wafer W or the substrate during a fabrication process. The stage element 3500 may include any one of stage devices according to various embodiments of the inventive concept, such as those described above. Therefore, the stage element 3500 may precisely control the wafer W or the substrate. Accordingly, in the measurement apparatus 3000 according to an embodiment of the inventive concept, reliability in the measured surface may be improved.

A stage device and a driving method thereof according to an embodiment of the inventive concept may include an interferometer disposed on a stage, an interference reflector disposed on a stage base, and an optical movable element configured to move a path of a beam emitted toward the interferometer according to a location of the stage. Therefore, in a stage device and driving method thereof according to an embodiment of the inventive concept, deformation of and damage to the interference reflector by stage movement may be prevented. Therefore, in a stage device and driving method thereof according to an embodiment of the inventive concept, reliability in the control of the stage may be improved. Further, in stage device and the driving method thereof according to an embodiment of the inventive concept, the total size may be reduced.

The foregoing is illustrative of embodiments and is not to be construed as limiting thereof. Although a few exemplary embodiments have been described, those skilled in the art will readily appreciate that many modifications are possible in exemplary embodiments without materially departing from the novel teachings. Accordingly, all such modifications are intended to be included within the scope of this inventive concept as defined in the claims.

What is claimed is:

1. A stage device comprising:
   a stage configured to move in an X-axis direction and a Y-axis direction;
   an X-axis interference reflector spaced apart from the stage in the X-axis direction;
   a first X-axis interferometer disposed on the stage that is configured to measure an X-axis location of the stage using the X-axis interference reflector; and
   an optical movable element spaced apart from the stage in the Y-axis direction that is configured to shift in the X-axis direction a path of a light beam propagating in the Y-axis direction, according to a movement of the stage in the X-axis direction.

2. The stage device of claim 1, wherein the optical movable element comprises an optical body that includes an optical guide groove extending in the X-axis direction, a supporting protrusion coupled to the optical guide groove, a supporting plate coupled to the supporting protrusion, and a driving element configured to move the supporting protrusion along the optical guide groove.

3. The stage device of claim 1, further comprising:
   a second X-axis interferometer disposed on the stage that is configured to measure the X-axis location of the stage using the X-axis interference reflector; and
   an X-axis beam splitter disposed on the stage that is configured to distribute the light beam propagating in the Y-axis direction toward the first X-axis interferometer and toward the second X-axis interferometer.

4. The stage device of claim 3, further comprising an X-axis fixed reflector disposed on the stage in a path of a light beam that has propagated through the X-axis beam splitter,
   wherein the first X-axis interferometer is disposed on a path of a light beam reflected by the X-axis fixed reflector, and the second X-axis interferometer is disposed on a path of a light beam reflected by the X-axis beam splitter.

5. The stage device of claim 3, wherein an X-axis distance between the first X-axis interference reflector and the second X-axis interferometer is the same as an X-axis distance between the first X-axis interference reflector and the first X-axis interferometer.

6. The stage device of claim 1, further comprising:
   a light source configured to emit a light beam in the X-axis direction, the light source being spaced from the stage in the Y-axis direction and;
   an optical element mounted on the optical movable element that is configured to distribute the light beam emitted from the light source in the X-axis direction and the Y-axis direction;
   a Y-axis interference reflector disposed on the stage; and
   a first Y-axis interferometer spaced from the stage in the Y-axis direction that is configured to measure a Y-axis location of the stage using the Y-axis interference reflector,
   wherein the optical element includes a beam splitter disposed between the light source and the first Y-axis interferometer that is configured to distribute in the X-axis direction and the Y-axis direction the light beam emitted from the light source, wherein the first X-axis interferometer is disposed between the X-axis interference reflector and the Y-axis interference reflector.

7. The stage device of claim 6, wherein the X-axis interference reflector extends in the Y-axis direction, and the Y-axis interference reflector extends in the X-axis direction,
   wherein a horizontal X-axis length of the Y-axis interference reflector is less than a horizontal Y-axis length of the X-axis interference reflector.

8. The stage device of claim 6, further comprising:
   a second Y-axis interferometer spaced apart from the stage in the Y-axis direction that is configured to measure the Y-axis location of the stage using the Y-axis interference reflector; and
   a Y-axis beam splitter spaced apart from the stage in the Y-axis direction that is configured to distribute a beam emitted from the light source in the X-axis direction toward the first Y-axis interferometer and toward the second Y-axis interferometer.

9. The stage device of claim 8, further comprising a Y-axis fixed reflector disposed on a path of a light beam that has propagated through the Y-axis beam splitter,
   wherein the first Y-axis interferometer is disposed on a path of a light beam reflected by the Y-axis fixed reflector, and the second Y-axis interferometer is disposed on a path of a light beam reflected by the Y-axis beam splitter.

10. The stage device of claim 8, wherein a Y-axis distance between the Y-axis interference reflector and the second Y-axis interferometer is the same as a Y-axis distance between the Y-axis interference reflector and the first Y-axis interferometer.

11. A stage device, comprising:
    a stage that includes a first X-axis interferometer, a first Y-axis interferometer spaced apart from the first X-axis interferometer, and a stage beam splitter configured to distribute a light beam toward the first X-axis interferometer and toward the first Y-axis interferometer;

a stage base configured to move the stage in an X-axis direction and a Y-axis direction;
a light source configured to emit a light beam in the X-axis direction;
a movable reflector configured to reflect the light beam emitted from the light source in the Y-axis direction; and
an optical movable element configured to move the movable reflector in the X-axis direction,
wherein the light source, the movable reflector and the optical movable element are disposed on the stage base, and the stage beam splitter is disposed on a path of the light beam reflected by the movable reflector.

12. The stage device of claim 11, wherein the stage further includes a second Y-axis interferometer spaced apart from the first Y-axis interferometer in the X-axis direction, a Y-axis fixed reflector configured to reflect a light beam to the first Y-axis interferometer, and a Y-axis beam splitter configured to distribute to the second Y-axis interferometer and the Y-axis fixed reflector the beam propagating toward the first Y-axis interferometer from the stage beam splitter, wherein a virtual line between the first Y-axis interferometer and the second Y-axis interferometer is parallel to an X-axis side of the stage base.

13. The stage device of claim 11, wherein the stage further includes a second X-axis interferometer spaced apart from the first X-axis interferometer in the Y-axis direction, a X-axis fixed reflector configured to reflect a light beam to the first X-axis interferometer, and a X-axis beam splitter configured to distribute to the second X-axis interferometer and to the X-axis fixed reflector the light beam propagating toward the first X-axis interferometer from the stage beam splitter,
wherein a virtual line between the first X-axis interferometer and the second X-axis interferometer is parallel to a Y-axis side of the stage base.

14. A stage device comprising:
a stage configured to move in an X-axis direction and a Y-axis direction;
a stage base configured to move the stage in an X-axis direction and a Y-axis direction;
an X-axis interference reflector mounted on the stage base and spaced apart from the stage in the X-axis direction;
a first X-axis interferometer disposed on the stage that is configured to measure an X-axis location of the stage using the X-axis interference reflector;
a Y-axis interference reflector that extends perpendicular to the X-axis interference reflector;
a first Y-axis interferometer configured to measure an Y-axis location of the stage using the Y-axis interference reflector; and
a beam splitter configured to distribute a light beam in the X-axis direction toward the first Y-axis interferometer and the Y-axis direction toward the first X-axis interferometer,
wherein the beam splitter shifts in the X-axis direction according to a movement of the stage in the X-axis direction.

15. The stage device of claim 14, wherein the Y-axis interference reflector is disposed on the stage base and is spaced apart from the stage in the Y-axis direction, the first Y-axis interferometer and the beam splitter are disposed on the stage.

16. The stage device of claim 15, further comprising:
a second Y-axis interferometer disposed on the stage and spaced apart from the first Y-axis interferometer in the X-axis direction; and
a Y-axis beam splitter and a Y-axis fixed reflector each disposed on the stage,
wherein the Y-axis beam splitter is configured to distribute a light beam received from the beam splitter to the second Y-axis interferometer and the Y-axis fixed reflector, and
the Y-axis fixed reflector is configured to reflect a light beam received from the Y-axis beam splitter to the first Y-axis interferometer,
wherein a virtual line between the first Y-axis interferometer and the second Y-axis interferometer is parallel to an X-axis side of the stage base.

17. The stage device of claim 15, further comprising:
a second X-axis interferometer disposed on the stage and spaced apart from the first X-axis interferometer in the Y-axis direction; and
an X-axis beam splitter and an X-axis fixed reflector each disposed on the stage,
wherein the X-axis beam splitter is configured to distribute a light beam received from the beam splitter to the second X-axis interferometer and to the X-axis fixed reflector, and
the X-axis fixed reflector is configured to reflect a light beam received from the X-axis beam splitter to the first X-axis,
wherein a virtual line between the first X-axis interferometer and the second X-axis interferometer is parallel to a Y-axis side of the stage base.

18. The stage device of claim 14, wherein the Y-axis interference reflector is disposed on the stage, the first Y-axis interferometer is disposed on the stage base and is spaced apart from the stage in the Y-axis direction, and further comprising:
a movable optical element upon which the beam splitter is mounted that is disposed on the stage base and spaced apart from the stage in a Y-axis direction, wherein the movable optical element is configured to move in the X-axis direction and the beam splitter is configured to distribute a light beam received from a light source.

19. The stage device of claim 18, further comprising:
a second X-axis interferometer disposed on the stage that is configured to measure the X-axis location of the stage using the X-axis interference reflector;
an X-axis beam splitter disposed on the stage that is configured to distribute a light beam received from the beam splitter toward the first X-axis interferometer and toward the second X-axis interferometer; and
an X-axis fixed reflector disposed on the stage in a path of a light beam that has propagated through the X-axis beam splitter,
wherein the first X-axis interferometer is disposed on a path of a light beam reflected by the X-axis fixed reflector, and the second X-axis interferometer is disposed on a path of a light beam reflected by the X-axis beam splitter, and an X-axis distance between the first X-axis interference reflector and the second X-axis interferometer is the same as an X-axis distance between the first X-axis interference reflector and the first X-axis interferometer.

20. The stage device of claim 18, further comprising:
a second Y-axis interferometer spaced disposed on the stage base and apart from the stage in the Y-axis direction that is configured to measure the Y-axis location of the stage using the Y-axis interference reflector;
a Y-axis beam splitter disposed on the stage base and spaced apart from the stage in the Y-axis direction that is configured to distribute a beam received from the beam splitter in the X-axis direction toward the first Y-axis interferometer and toward the second Y-axis interferometer; and a Y-axis fixed reflector disposed on the stage base on a path of a light beam that has propagated through the Y-axis beam splitter, wherein the first Y-axis interferometer is disposed on a path of a light beam reflected by the Y-axis fixed reflector, and the second Y-axis interferometer is disposed on a path of a light beam reflected by the Y-axis beam splitter, and a Y-axis distance between the Y-axis interference reflector and the second Y-axis interferometer is the same as a Y-axis distance between the Y-axis interference reflector and the first Y-axis interferometer.

* * * * *